US010751408B2

(12) United States Patent
Randolph et al.

(10) Patent No.: US 10,751,408 B2
(45) Date of Patent: Aug. 25, 2020

(54) COMPOSITIONS AND METHODS FOR MAKING AND USING THERMOSTABLE IMMUNOGENIC FORMULATIONS WITH INCREASED COMPATIBILITY OF USE AS VACCINES AGAINST ONE OR MORE PATHOGENS

(71) Applicant: The Regents of the University of Colorado, a body corporate, Denver, CO (US)

(72) Inventors: Theodore W. Randolph, Niwot, CO (US); Robert Garcea, Boulder, CO (US); Alan W. Weimer, Niwot, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 0 days.

(21) Appl. No.: 16/079,507

(22) PCT Filed: Feb. 23, 2017

(86) PCT No.: PCT/US2017/019163
§ 371 (c)(1),
(2) Date: Aug. 23, 2018

(87) PCT Pub. No.: WO2017/147318
PCT Pub. Date: Aug. 31, 2017

(65) Prior Publication Data

US 2019/0046632 A1 Feb. 14, 2019

Related U.S. Application Data

(60) Provisional application No. 62/404,408, filed on Oct. 5, 2016, provisional application No. 62/381,558, filed on Aug. 30, 2016, provisional application No. 62/298,912, filed on Feb. 23, 2016.

(51) Int. Cl.
| | |
|---|---|
| *G01N 27/403* | (2006.01) |
| *C12Q 1/68* | (2018.01) |
| *G01N 27/414* | (2006.01) |
| *C12M 1/34* | (2006.01) |
| *C12M 3/00* | (2006.01) |
| *A61K 39/12* | (2006.01) |
| *A61K 9/50* | (2006.01) |
| *A61K 39/02* | (2006.01) |
| *A61K 39/39* | (2006.01) |
| *A61K 39/00* | (2006.01) |

(52) U.S. Cl.
CPC ............ *A61K 39/12* (2013.01); *A61K 9/5015* (2013.01); *A61K 39/02* (2013.01); *A61K 39/39* (2013.01); *A61K 2039/55505* (2013.01); *A61K 2039/55555* (2013.01); *A61K 2039/60* (2013.01); *C12N 2710/20034* (2013.01); *C12N 2770/24134* (2013.01)

(58) Field of Classification Search
CPC .. G01N 27/4145; G01N 27/27; G01N 27/414; C12Q 1/6874; C12Q 1/6869
See application file for complete search history.

(56) References Cited

FOREIGN PATENT DOCUMENTS

| | | | |
|---|---|---|---|
| EP | 1516615 | A2 * | 8/1995 |
| EP | 1516615 | A2 * | 3/2005 |
| EP | 2829282 | B1 | 1/2015 |
| WO | 03/032945 | A1 | 4/2003 |
| WO | 2009015286 | A3 | 1/2009 |

OTHER PUBLICATIONS

Hassett et al. Development of a Highly Thermostable, Adjuvanted Human Papillomavirus Vaccine; European Journal of Pharmaceutics and Biopharmaceutics 94 (2015) 220-228.
Hassett, Kimberly J. "Stabilization of a Recombinant Ricin Toxin a Subunit Vaccine Through Lyophilization." European Journal of Parmaceutics and Biopharmaceutics, 85:279-286, 2013.
International Search Report and Written Opinion issued in PCT/US2017/019163, dated Jun. 7, 2017, 16 pages.
Sharma et al. PLGA-Based Nanoparticles: A New Paradigm in Biomedical Applications; Trends in Analytical Chemistry 80 (2016) 30-40.

* cited by examiner

*Primary Examiner* — Barry A Chestnut
(74) *Attorney, Agent, or Firm* — Polsinelli PC

(57) ABSTRACT

Embodiments of the present disclosure provide novel compositions, methods of use and methods for single composition, multi-dose, thermostable vaccine formulations. In certain embodiments, the present disclosure provides compositions and methods for dehydrating immunogenic agents in the presence of glass-forming agents, and coating the particles formed by the glass-forming agents. In other embodiments, the present disclosure provides for generating compositions for administering an immunogenic composition to a subject multiple times using a single immunogenic composition capable of time-release administration. In other embodiments, single-dose immunogenic agent-containing particles can be directed to two or more pathogens. In other embodiments, incompatible immunogenic agents against two or more different pathogens of immunogenic agent-containing particles disclosed herein can be mixed together and coated for timed-release administration to produce single-administration formulations capable of eliciting an immune response to the two or more pathogens in a subject.

23 Claims, 10 Drawing Sheets

Binary Reaction Sequence for Alumina ALD

COMPOSITIONS AND METHODS FOR MAKING AND USING THERMOSTABLE IMMUNOGENIC FORMULATIONS WITH INCREASED COMPATIBILITY OF USE AS VACCINES AGAINST ONE OR MORE PATHOGENS

RELATED APPLICATIONS

This international application claims priority to U.S. Provisional Application No. 62/298,912, filed Feb. 23, 2016, U.S. Provisional Application No. 62/381,558, filed Aug. 30, 2016, and U.S. Provisional Application No. 62/404,408, filed Oct. 5, 2016, each of which is incorporated herein by reference in their entireties for all purposes.

FIELD

Embodiments of the present disclosure provide novel compositions and methods for making and using thermostable immunogenic formulations. In certain embodiments, compositions and methods are disclosed for embedding immunogenic agents in an organic glassy matrix of a glass-forming agent and coating the resulting immunogenic agent-containing glassy microparticle with one or more coating layers to produce an immunogenic agent-containing particle for use in a formulation. In other embodiments, the immunogenic agent-containing particles can increase stability and/or compatibility of the immunogenic agents and/or provide for time-release delivery of the immunogenic agents. In some embodiments, primary and boost doses of an immunogenic agent found in immunogenic agent-containing particles can be administered to a subject in a single administration. In other embodiments, immunogenic agent-containing particles can include immunogenic agents against two or more pathogens either in the same or in separate particles. Immunogenic agent-containing particles disclosed herein can be directed to different pathogens, and can be mixed together to produce a single, multi-immunogenic formulation against the different pathogens.

BACKGROUND

Therapeutic impacts of vaccines can be compromised by many challenges. One challenge is the delivery of a vaccine to a subject. For example, multiple administrations are often required to provide successful immunity, which can decrease the likelihood that a subject will take the necessary steps to obtain a required second or more administrations. In addition, vaccines and vaccine formulations often exhibit increased instability during storage, transport and handling, and the vaccine supply chain can require expensive and logistically complex refrigeration (e.g., cold chain requirements). Further, certain vaccines against a particular pathogen must be separately administered at the same time or at different times to a subject to avoid being ineffective when combined or administered at the same time as another vaccine against another pathogen. Additionally, vaccines and vaccine formulations are typically associated with high manufacturing costs, which can limit their availability to those in need.

SUMMARY

Embodiments of the present disclosure provide novel compositions and methods for making and using thermostable immunogenic formulations. In certain embodiments, compositions and methods are disclosed for embedding immunogenic agents in an organic glassy matrix of a glass-forming agent and coating the resulting immunogenic agent-containing glassy microparticle with one or more coating layers to produce an immunogenic agent-containing particle for use in a formulation. In other embodiments, the immunogenic agent-containing particles can increase stability and/or compatibility of the immunogenic agents and/or provide for time-release delivery of the immunogenic agents. In some embodiments, primary and boost doses of an immunogenic agent found in immunogenic agent-containing particles can be administered to a subject in a single administration. In other embodiments, immunogenic agent-containing particles can include immunogenic agents against two or more pathogens either in the same or in separate particles.

In accordance with these embodiments, immunogenic agent-containing particles disclosed herein have a central or innermost immunogenic agent-containing glassy microparticle including at least one immunogenic agent and at least one glass-forming agent, and one or more outer coating layers covering or encasing the central immunogenic agent-containing glassy microparticle. In accordance with these embodiments, one, two, three, four, five or more coating layers can encase the immunogenic agent-containing particles wherein the coating layers are readily dissolvable in a subject once administered, to expose the immunogenic agent-containing particles to the subject.

Certain embodiments of the present disclosure provide methods for making the immunogenic agent-containing particles, the method including combining at least one immunogenic agent with at least one glass-forming agent to form a primary liquid immunogenic composition, dehydrating the primary liquid immunogenic composition to form immunogenic agent-containing glassy microparticles, and coating the immunogenic agent-containing glassy microparticles with one or more outer coating layers. In some embodiments, the primary liquid immunogenic composition can be dehydrated by lyophilization, vacuum-drying, spray drying, or spray-freeze-drying.

In accordance with these embodiments, the at least one immunogenic agent can include one or more antigens, for example a viral antigen, a bacterial antigen, a toxin, or a combination thereof. In some embodiments, the at least one immunogenic agent can also include but is not limited to, a recombinant peptide, a recombinant protein, a peptide derived from a target protein or pathogen, a synthetic peptide or protein, a virus-like particle, a live virus, a live, attenuated virus, an inactivated virus, or a combination thereof.

In certain embodiments, the at least one immunogenic agent can include one or more antigens for example, antigens derived from human papilloma virus, ricin toxin, *Bacillus anthraces, Clostridium botulinum*, Ebola virus, poliovirus, norovirus, rotavirus, hepatitis C, varicella, herpes simplex, cytomegalovirus, Japanese encephalitis, dengue virus, West Nile virus, Zika virus, *Yersinia, Pneumococcus, Salmonella, Clostridium difficile*, or a combination thereof. In certain embodiments, the at least one immunogenic agent can be a multimeric complex.

In some embodiments, the at least one glass-forming agent can include at least one of trehalose, sucrose, ficoll, dextran, sucrose, maltotriose, lactose, mannitol, hydroxyethyl starch, glycine, cyclodextrin, povidone, or the like. In certain embodiments, the at least one glass-forming agent can include trehalose. In accordance with this embodiment, trehalose can be included as a glass-forming agent and can be present in the primary liquid immunogenic composition in a weight-to-volume (w/v) concentration of from about 0.1% to about 40%, from about 1% to about 30%, from about 5% to about 20%, or from about 8% to about 15%.

In other embodiments, the glass-forming agent also includes at least one smoothing excipient. In accordance with these embodiments, the smoothing excipient can be a hydroxyethyl starch or other pharmacologically acceptable plasma expander such as human serum albumin (HSA), other serum albumins, dextran, hetastarch, plasma protein factor and the like, or a combination thereof. In certain embodiments, the smoothing excipient can also be the primary glass-forming agent. In particular embodiments, the smoothing excipient is hydroxyethyl starch. In some embodiments, a smoothing agent disclosed herein can be the primary glass-forming agent. In accordance with these embodiments, the smoothing excipient can be present in the primary immunogenic composition at a weight-to-volume (w/v) concentration from about 0.1% to about 40%, from about 1% to about 30%, from about 5% to about 20%, or from about 8% to about 15%. In certain embodiments, the smoothing excipient can be different than the primary glass-forming agent, and the smoothing excipient can be present in the primary immunogenic composition in a weight-to-volume (w/v) concentration from about 0.1% to about 10%, from about 0.1% to about 5%, from about 0.1% to about 2.5%, from about 0.1% to about 0.5%. In certain embodiments, the glass-forming agent present in the immunogenic composition is trehalose and the smoothing excipient for the particles is hydroxyethyl starch.

In some embodiments, each layer of the one or more outer coating layers can include aluminum oxide, an aluminum alkoxide (e.g., alucone), silicon dioxide ($SiO_2$), titanium dioxide ($TiO_2$), or silicon nitride ($Si_3N_4$) alone or in a suitable combination composition. In accordance with these embodiments, the outer coating layer(s) can be about 0.1 nm to about 20 nm in thickness. In certain embodiments, the immunogenic agent-containing particle can include a number of outer coating layers sufficient to delay release or provide a timed-release of the at least one immunogenic agent from the central or innermost immunogenic agent-containing glassy microparticle.

In certain embodiments, the one or more coating layer(s) disclosed herein can serve as an adjuvant to enhance the immune response in a subject against one or more immunogenic agent(s) of the immunogenic agent-containing particle. In certain embodiments, the one or more coating layer(s) can contain a concentration capable of inducing a rapid immune response to the one or more immunogenic agent(s) of the immunogenic agent-containing particle.

In other embodiments, the immunogenic agent-containing particle can further include at least a second immunogenic agent deposited as a layer on an outermost coating layer of the immunogenic agent-containing particle. In accordance with these embodiments, the layer of the at least the second immunogenic agent can be embedded in a glassy matrix of at least a second glass-forming agent to stabilize the second immunogenic agent. In other embodiments, methods for producing at least one layer of the at least a second immunogenic agent and embedding the second immunogenic agent in a glassy matrix of at least a second glass forming agent are also provided. In some embodiments, at least one additional outer coating layer covers or encases the layer of the at least second immunogenic agent. In certain embodiments, the second immunogenic agent is identical to the at least one immunogenic agent of the central immunogenic agent-containing glassy microparticle. In other embodiments, the second immunogenic agent is different than the at least one immunogenic agent of the central immunogenic agent-containing glassy microparticle.

In some embodiments, immunogenic agent-containing particles described herein can be stored without refrigeration temperatures of up to about 50° C. to about 60° C. for extended periods of time. In certain embodiments, immunogenic agent-containing particles described herein can be stored without refrigeration up to about 50° C. to about 60° C. up to about 3 months, or up to about 4 months, or up to about 6 month, or up to about 9 months, or up to about 12 months, or up to about 15 months, or up to about 18 months, or up to about 24 months or longer without negative effect on the immunogenic agent-containing particles (e.g. degradation)

Other embodiments of the present disclosure provide for immunogenic compositions including a plurality of immunogenic agent-containing particles described herein. In certain embodiments, the immunogenic composition can include immunogenic agent-containing particles in a pharmaceutically acceptable excipient to make a pharmaceutically acceptable immunogenic composition. In accordance with these embodiments, immunogenic compositions described herein are capable of eliciting an immune response to the immunogenic agent when administered to a subject.

In some embodiments, the immunogenic composition is a single-administration immunogenic composition comprising a prime dose and boost dose of at least one immunogenic agent. In accordance with these embodiments, the prime and boost doses of the at least one immunogenic agent can be in the same immunogenic agent-containing particle, or in separate immunogenic agent-containing particles. When in separate particles, the priming dose of the at least one immunogenic agent can be sequestered in an immunogenic agent-containing glassy microparticle without any outer coating layers, or in an immunogenic agent-containing particle, while the boost dose of the at least one immunogenic agent is in another immunogenic agent-containing particle. Whether the priming dose is in an immunogenic agent-containing glassy microparticle or in an immunogenic agent-containing particle will be determined by whether an immediate or delayed response is desired, where outer coating layers of an immunogenic agent-containing particle sequestering the prime dose will temporally delay release of the priming dose, and therefore, delay exposure of the priming dose to the subject.

In some embodiments, the immunogenic composition can be a single administration immunogenic composition capable of eliciting an immune response to two or more different immunogenic agents. In accordance with these embodiments, the two or more different immunogenic agents can be included in the same immunogenic agent-containing particles, or in separate immunogenic agent-containing particles. In other embodiments, when the two or more different immunogenic agents are contained in separate immunogenic agent-containing particles, each different immunogenic agent-containing particle comprises a different immunogenic agent or combinations of immunogenic agents.

In some embodiments, an immunogenic composition can include prime and boost doses of a first immunogenic agent and prime and boost doses of a second immunogenic agent. In accordance with these embodiments, the prime and boost doses of the first immunogenic agent are in a first immunogenic agent containing particle, while the prime and boost doses of the second immunogenic agent are sequestered in a second immunogenic agent-containing particle. In other embodiments, the prime and boost doses of the first immunogenic agent are located in a first pair of particles, the prime dose being in a separate particle from the boost dose, and the prime and boost doses of the second immunogenic agent are sequestered in a second pair of particles, the prime dose being in a separate particle from the boost dose, where the prime dose for each of the first and second immunogenic agent are in separate immunogenic agent-containing glassy microparticles and the boost dose for each the first and second immunogenic agent are in separate immunogenic agent-containing particles. In yet other embodiments, the prime and boost doses of the first immunogenic agent are sequestered in a first pair of immunogenic agent-containing particles, the prime dose being in a separate particle from the boost dose, and the prime and boost doses of the second immunogenic agent are located in a second pair of immunogenic agent-containing particles, the prime dose being in a separate particle from the boost dose, wherein the prime dose for the first immunogenic agent is in an immunogenic agent-containing glassy microparticle, the prime dose for the second antigen is in a separate immunogenic agent-containing particle, and the boost dose for each the first and second antigen are in separate immunogenic agent-containing particles.

In other embodiments, an immunogenic composition can include a standard vaccine composition and a plurality of immunogenic agent-containing particles described, wherein the at least one immunogenic agent elicits a boost immune response to the standard vaccine composition.

In yet other embodiments, an immunogenic composition can include a plurality of first immunogenic agent-containing particles described herein, wherein the first immunogenic agent-containing particles can include at least a first immunogenic agent, a plurality of second immunogenic agent-containing particles described herein, wherein the second immunogenic agent-containing particles includes at least a second immunogenic agent different than the first immunogenic agent, and a pharmaceutically acceptable excipient. In accordance with embodiments, the immunogenic composition can further include a plurality of at least one additional immunogenic agent-containing particles described herein, wherein the at least one additional immunogenic agent-containing particles include at least one additional immunogenic agent that is not the first immunogenic agent or the second immunogenic agent.

Other embodiments provide for methods for eliciting an immune response in a subject, where the method can include administering an immunogenic composition described herein to the subject. In accordance with these embodiments, the immunogenic composition can induce an immune response in the subject. The immune response induced by the immunogenic composition can be prophylactic or therapeutic depending on the immunogenic agent.

Yet other embodiments provide for kits that can include at least one immunogenic agent-containing particle described herein and at least one apparatus capable of an immunogenic composition disclosed herein to a subject.

BRIEF DESCRIPTION OF THE FIGURES

The accompanying drawings are incorporated into and form a non-limiting part of the specification to illustrate several examples of the present disclosure.

DETAILED DESCRIPTION

Figure 1A:
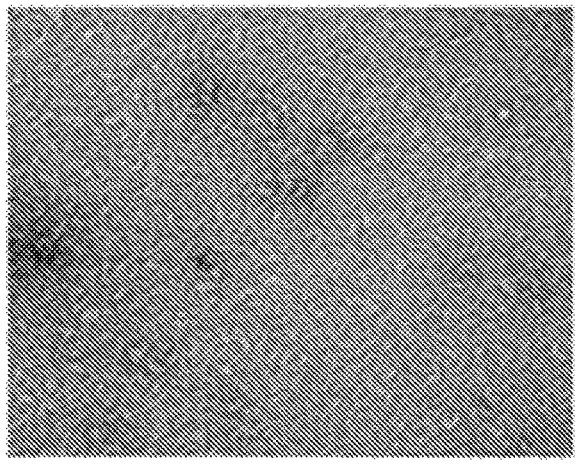
FIGS. 1A-1C are representative electron micrographs of HPV L1 capsomeres before lyophilization (A), immediately after lyophilization and reconstitution (B), and after storage in the lyophilized state and reconstituted (C), according to one embodiment of the present disclosure.

In the following sections, various exemplary compositions and methods are described in order to detail various embodiments. It will be obvious to one skilled in the art that practicing the various embodiments does not require the employment of all or even some of the specific details outlined herein, but rather that concentrations, times and other specific details may be modified through routine experimentation. In some embodiments, well known methods or components have not been included in the description.

Embodiments of the present disclosure provide novel compositions, methods of use and methods for making single immunogenic compositions as multi-dose, thermostable vaccine formulations. In certain embodiments, the present disclosure provides compositions and methods for dehydrating immunogenic agents in the presence of glass-forming compounds, and generating single-dose immunogenic agent-containing particles having one or more coating layers. In some embodiments, immunogenic agents can be dehydrated by lyophilization, vacuum-drying, spray drying, or spray-freeze-drying.

In other embodiments, the present disclosure provides for compositions and methods for vaccinating a subject using single administration of a single immunogenic composition capable of time-release of the immunogenic agents to the subject. In other embodiments, a single-dose immunogenic composition can be directed to two or more pathogens either in the same or in separate immunogenic agent-containing particles. In accordance with these embodiments, immunogenic agent-containing particles directed to different pathogens can be mixed together to produce single-administration formulations capable of eliciting an immune response in a subject to two or more pathogens. In accordance with these embodiments, any immunogenic-containing particle can be mixed with another immunogenic-containing particle for delivery to a subject. For example, immunogenic agents that typically create immune interference when introduced together in a subject or other incompatibility can be combined and delivered in a single immunogenic composition to a subject. In certain embodiments, incompatible agents used in immunogenic-containing particles can be by a time-released manner using the dehydrating and coating methods and compositions disclosed herein.

In certain embodiments, immunogenic agent-containing particles and immunogenic compositions disclosed herein can use less immunogenic agent than used to formulate current vaccines against the immunogen (e.g., cost saving), and provide enhanced efficacy after a single administration. In other embodiment, immunogenic agent-containing particles provide for thermostable formulations that eliminate and/or reduce refrigeration requirements (e.g., cold chain refrigeration requirements), limit the amount of adverse agents (e.g. aluminum) administered to subjects, and increase immunogenic agent compatibility. In other embodiments, compositions and methods disclosed herein are applicable to a variety of potential antigens, including, but not limited to, recombinant peptide or protein immunogens, virus-like particles (VLPs), and inactivated or attenuated pathogens (e.g. viruses).

Some embodiments disclosed herein relate methods of dehydration and formulation parameters, where these parameters can be adjusted in order to control nucleation rates, glass transition temperatures, and other material properties of the immunogenic agent-containing glassy microparticles (see, e.g., FIGS. 1A-1C and FIGS. 2A-2B, uncoated). In certain embodiments, dehydration of immunogenic agents can occur, for example, by lyophilization, vacuum-drying, spray drying, and/or spray-freeze-drying. In accordance with these embodiments, the immunogenic agent-containing glassy microparticles can be encased with one or more coating layers to produce immunogenic agent-containing particles (coated particles). In other embodiments, immunogenic agent-containing particles having immunogenic agents directed to one or more pathogens, either in the same particle or in separate particles, can be combined into an aqueous solution to produce an immunogenic formulation. These immunogenic agent-containing particles described herein are thermostable and can be generated against any pathogenic agent. In certain embodiments, immunogenic agent-containing particles can be generated against any pathogenic virus.

In certain embodiments, the pathogenic virus may be, for example, a papovavirus (e.g., papillomaviruses, including human papilloma virus (HPV)), a herpesvirus (e.g., herpes simplex virus, varicella-zoster virus, bovine herpesvirus-1, cytomegalovirus), a poxvirus (e.g., smallpox virus), a reovirus (e.g., rotavirus), a parvovirus (e.g., parvovirus B19, canine parvovirus), a picornavirus (e.g., poliovirus, hepatitis A), a togavirus (e.g., rubella virus, alphaviruses such as chikungunya virus), a hepadnavirus (e.g., hepatitis B virus), a flavivirus (e.g., dengue virus, hepatitis C virus, West Nile virus, yellow fever virus, Zika virus, Japanese encephalitis virus), an orthomyxovirus (e.g., influenza A virus, influenza B virus, influenza C virus), a paramyxovirus (e.g., measles virus, mumps virus, respiratory syncytial virus, canine distemper virus, parainfluenza viruses), a rhabdovirus (e.g., rabies virus), a filovirus (e.g., Ebola virus), or a coronavirus or combinations thereof.

In other embodiments, the pathogenic agent can be a bacterium or a toxin of a bacterium, including but not limited to, *Pasteurella haemolytica, Clostridium difficile, Clostridium haemolyticum, Clostridium tetani, Corynebacterium diphtheria, Neorickettsia resticii, Streptococcus equi equi, Streptococcus pneumoniae, Salmonella* spp., *Chlamydia trachomatis, Bacillus anthraces, Yersinia* spp., and *Clostridium botulinum* or combinations thereof.

In some embodiments, the pathogenic agent can be a fungus, including but not limited to *Cryptococcus* spp. (e.g.,

*neoformans* and *gatti*), *Aspergillus* spp. (e.g., *fumigatus*), *Blastomyces* spp. (e.g., dermatitidis), *Candida albicans, Paracoccidioides* spp. (e.g., *brasiliensis*), *Sporothrix* spp. (e.g., *schenkii* and *brasiliensis*), *Histoplasma capsulatum, Pneumocystis jirovecii* and *Coccidioides immitis*, or combinations thereof.

In yet other embodiments, the pathogenic agent may be a toxin, such as ricin toxin or botulinum toxin.

In some embodiments, immunogenic agent-containing particles described herein may be used to manufacture one or more immunogenic composition of use as vaccines for animals such as household pets. In accordance with these embodiments, the immunogenic composition can be administered, for example, to a dog (canine), a cat (feline), a horse (equine), cattle (bovine), a goat (hircine), a sheep (caprine), or poultry (e.g., chicken, turkey, duck, goose).

In certain embodiments, immunogenic agent-containing particles described herein can be used to generate one or more immunogenic compositions for administering to a canine to reduce onset of or prevent an infection , including but not limited to, infections related to canine parvovirus (CPV), canine distemper virus (CDV), canine adenovirus (CAV), rabies, canine parainfluenza virus (CPiV), canine influenza virus, canine corona virus, measles virus, *Bordetella bronchiseptica, Leptospira* spp., and *Borrelia burgdorferi* or combinations thereof.

In some embodiments, immunogenic agent-containing particles described herein may be used to generate immunogenic compositions of use for administering to a feline to reduce or prevent an infection or treat an infection, including but not limited to, immunogenic compositions directed to feline herpesvirus 1 (FHV1), feline calicivirus (FCV), feline panleukopenia virus (FPV), rabies, feline leukemia virus (FeLV), feline immunodeficiency virus, virulent systemic feline calicivirus, *Chlamydophila felis, Pasteurella haemolytica*, and *Bordetella bronchiseptica* or combinations thereof.

In other embodiments, immunogenic agent-containing particles described herein may be used to generate immunogenic compositions of use for administering to equine, to reduce or prevent an infection or treat an infection, including but not limited to, immunogenic compositions directed to Eastern equine encephalomyelitis virus, Western equine encephalomyelitis virus, Venezuelan equine encephalomyelitis virus, bovine papillomavirus, rabies virus, *Clostridium tetani*, West Nile virus, equine influenza virus, Potomac fever (*Neorickettsia risticii*), *Streptococcus equi equi*, and rhinopneumonitis (equine herpesvirus type 1) or combinations thereof.

In certain embodiments, immunogenic agent-containing particles described herein may be used to generate immunogenic compositions of use for administering to bovine, to reduce or prevent an infection or treat an infection, including but not limited to, immunogenic compositions directed to bovine rhinotracheitis (IBR), parainfluenza type 3 (PI3), bovine virus diarrhea (BVD), bovine respiratory syncytial virus (BRSV), blackleg (*Clostridium chauvoei*), malignant edema (*Clostridium septicum*), infectious necrotic hepatitis (*Clostridium novyi*), enterotoxemia (*Clostridium perfringens* type C and D), *Pasteurella haemolytica*, and redwater (*Clostridium haemolyticum*) or combinations thereof.

In some embodiments, immunogenic agent-containing particles described herein may be used to generate immunogenic compositions of use for administering to poultry, to reduce or prevent an infection or treat an infection, including but not limited to, immunogenic compositions directed to Marek's disease (Marek's disease virus), tenosynovitis (reoviruses), encephalomyelitis (avian encephalomyelitis virus), fowlpox (avipoxviruses), chicken infectious anemia (chicken anemia virus), fowl cholera (*Pasteurella multocida*), Newcastle/infectious bronchitis (Newcastle disease virus), *Riemerella anatipestifer*, duck viral hepatitis (duck hepatitis virus), and duck viral enteritis (duck herpesvirus 1) or combinations thereof.

In some embodiments, immunogenic agent-containing particles described herein may be used to generate immunogenic compositions of use for administering to a human. In certain embodiments, immunogenic agent-containing particles described herein may be used to deliver one or more immunogenic compositions to a human infant or child or adolescent, including but not limited to vaccines for varicella-zoster (chicken pox), diphtheria, *Haemophilus influenzae* type b (Hib), hepatitis A, hepatitis B, influenza, measles, mumps, pertussis, polio, pneumococcal disease, rotavirus, rubella, and tetanus. In other embodiments, immunogenic agent-containing particles described herein may be used to deliver one or more immunogenic compositions to a human pre-teen or teen, including but not limited to vaccines for influenza, tetanus, diphtheria, pertussis, human papillomavirus, meningococcal disease, hepatitis B, hepatitis A, polio, measles, mumps, rubella, and varicella-zoster. In yet other embodiments, immunogenic agent-containing particles described herein may be used to deliver one or more immunogenic compositions to a human adult, including but not limited to immunogenic compositions against influenza (e.g. A, B or C), tetanus, diphtheria, pertussis, zoster, pneumococcal disease, meningococcal disease, measles, mumps, rubella, varicella, hepatitis A, hepatitis B, and *Haemophilus influenzae* type b.

In other embodiments, immunogenic agent-containing particles described herein may be used to generate immunogenic compositions of use for administering to a human, including but not limited to, immunogenic compositions against travel-related diseases, including but not limited to hepatitis A, hepatitis B, typhoid fever, paratyphoid fever, meningococcal disease, yellow fever, dengue fever, rabies, Chikungunya disease, and Japanese encephalitis.

In yet other embodiments, immunogenic agent-containing particles described herein may be used to generate immunogenic compositions of use for administering to a human, including but not limited to, immunogenic compositions against human papillomavirus (e.g. HPV 16, HPV18, HPV31, HPV45, or HPV 6 or HPV11, or any other HPV), herpes simplex virus, smallpox virus, rotavirus, parvovirus B19 vaccine, chikungunya virus, dengue virus (e.g. dengue-1, dengue-2, dengue-3 or dengue-4) , hepatitis C virus, West Nile virus, Zika virus, respiratory syncytial virus, rabies virus, and Ebola virus.

In certain embodiments, immunogenic agent-containing particles described herein may include a single immunogenic agent dose or two or more doses of a particular immunogenic agent (e.g., prime and boost doses). In some embodiments, an immunogenic agent-containing particle may include doses for two or more different immunogenic agents. In yet other embodiments, immunogenic agent-containing particles including doses of different immunogenic agents may be combined into a mixture of immunogenic agent-containing particles. A mixture of immunogenic agent-containing particles may be combined into a single administration. This may result in a reduced number of required vaccine administrations.

In some embodiments, methods disclosed herein can concern controlled, ultra-rapid freezing rates combined with various concentrations of glass-forming agents. In accordance with these embodiments, glass-forming agents can include, but are not limited to, trehalose or sucrose. These agents can be used to generate glass-like matrices upon freezing. In certain embodiments, when the glass-forming agents are dried during a dehydration process (e.g., lyophilization) in the presence of one or more immunogenic agents, these form powders (immunogenic agent-containing glassy microparticles), containing embedded immunogenic agents. In this dehydrated state, protein physical and chemical degradation pathways, which require molecular motion, can be inhibited, as are other degradation pathways thereby stabilizing the immunogenic agent.

In other embodiments, one or more adjuvants and/or immune-stimulating agents can be incorporated into the immunogenic agent-containing glassy microparticles or layered onto the immunogenic agent-containing particles. In accordance with these embodiments, the adjuvant or co-adjuvant can be combined with the immunogenic agent and glass-forming agent prior to dehydration or used in an outer layer. Other methods can be used to dehydrate the glass-forming agents and immunogenic agents, for example, vacuum-drying, spray drying and spray-freeze-drying the agents.

In some embodiments, one or more immunogenic agents can be combined with a glass forming agent to produce an immunogenic composition. For example, the immunogenic composition can then be dehydrated to form immunogenic agent-containing glassy microparticles. In other embodiments, adjuvants and/or co-adjuvants can be included in the immunogenic composition in preparation for dehydration of the combination.

Immunogenic agent-containing glassy microparticles and methods for making the same are described in detail in the disclosures of U.S. Pat. Nos. 8,444,991 and 8,808,710, as well as A L Clausi et al., J Pharm Sci, 2008 June; 97(6): 2049-61, K J Hassett et al., Eur J Pharm Biopharm, 2013 October; 85(2):279-86, K J Hassett et al., J Pharm Sci, 2015 February; 104(2):627-39, and K J Hassett et al., Eur J Pharm Biopharm, 2015 August; 94:220-8, each of which is hereby incorporated in its entirety.

In some embodiments, immunogenic agents demonstrate considerable thermostability following incorporation into the glassy organic matrix formed by dehydrating the immunogenic composition (e.g., the mixture of immunogenic agent and glass forming agent). In other embodiments, thermostabilized immunogenic agent-containing glassy microparticles where the immunogenic agent is HPV16 L1 capsomeres can be incubated at 50° C. for at least 12 weeks without loss of immunogenicity (see, e.g., K J Hassett et al., Eur J Pharm Biopharm, 2015 August; 94:220-8, incorporated herein by reference). In some embodiments, thermostabilized immunogenic agent-containing glassy microparticles can be produced with candidate antigens disclosed herein. Candidate antigens can include but are not limited to, antigens of ricin toxin, *Bacillus anthracis, Clostridium botulinum*, human papilloma virus, Ebola virus, poliovirus, norovirus, rotavirus, hepatitis C, dengue virus, varicella, herpes simplex, cytomegalovirus, Japanese encephalitis, West Nile virus, Zika virus and other related viruses such other flaviviruses. In some embodiments, bacterial antigens can be included in immunogenic agent-containing glassy microparticles, such as, for example, antigens of *Pneumococcus, Salmonella*, and *Clostridium difficile*. In certain embodiments, the antigen can be a toxoid, such as, for example, ricin toxoid, tetanus toxoid, diphtheria toxoid, and botulinum toxoid. Various other immunogenic agents can be included in immunogenic agent-containing glassy microparticles, where the immunogenic agent is capable of undergoing transitions and reconstitutions as described herein, including antigens of other bacteria, viruses, fungi, or toxins.

Pathogenic agents and antigens derived therefrom contemplated herein can be in the form of recombinant peptide or protein immunogens, virus-like particles (VLPs), or inactivated or attenuated pathogens (e.g. viruses) or chimeric viruses or chimeric viruses in the same virus family such as flaviviruses, alphaviruses or the like. In certain embodiments, human papilloma virus (HPV) capsomeres can be incorporated into thermostable glassy microparticle via lyophilization without effect on the morphology of the HPV capsomeres. In certain embodiments, capsomeres from two or more HPV can be incorporated into the same glassy microparticle. For example, in some embodiments, capsomeres from HPV types 16, 18, and 31 can be incorporated into the same glassy microparticle to produce a trivalent glassy microparticle. In other embodiments, capsomeres from HPV types 16, 18, 31, and 45 can be incorporated into the same glassy microparticle to produce a tetravalent glassy microparticle. In certain embodiments, the capsomere from each HPV type is the L1 protein. Many different combinations of capsomeres from different HPV types can be incorporated into glassy microparticles. Recombinant peptides or protein immunogens from pathogens other than HPV can be incorporated into thermostable glassy microparticles, similarly to L1 HPV capsomeres.

In other embodiments, virus-like particles (VLPs) can be lyophilized into thermostable glassy microparticles. VLPs resemble viruses, but do not replicate and contain viral genetic material. Therefore, VLPs have been demonstrated to be useful in vaccine formulations, providing a safer alternative to attenuated viruses. They contain high density displays of viral surface proteins that present viral epitopes that can elicit strong immune responses. In certain embodiments, VLPs from pathogens other than HPV can be incorporated into thermostable glassy microparticle, similarly to HPV 16L1 VLP. Some non-limiting examples include VLPs of Hepatitis B, chikungunya virus, and influenza virus.

In yet other embodiments, inactivated or attenuated pathogens (e.g. live, attenuated viruses) can be lyophilized into thermostable glassy microparticles. In accordance with these embodiments, inactivated (or killed) viruses or virus particles, bacteria, or other pathogens may be inactivated by any means, for example, chemically or by heat and incorporated into thermostable glassy microparticles. Non-limiting examples of inactivated pathogens that may be incorporated into thermostable glassy microparticles can include inactivated whole-cell pertussis (inactivated *Bordetella pertussis*), *Salmonella typhi*, and inactivated polio virus. Live, attenuated viruses or bacteria may similarly be incorporated into thermostable glassy microparticles. Non-limiting examples of attenuated viruses and bacteria that may be incorporated into thermostable glassy microparticles can include measles virus, mumps virus, rubella virus, influenza virus, chicken pox virus, smallpox virus, polio virus, rotavirus, flaviviruses (e.g. dengue virus, yellow fever virus), rabies virus, typhoid virus, *Mycobacterium bovis, Salmonella typhi*, and *Rickettsia* spp.

In some embodiments, one or more agents supplementing the immunogenic composition, such as an adjuvant, can be included in a thermostable glassy microparticle that includes an immunogenic agent. In accordance with these embodiments, supplementing agents contemplated herein may include, but are not limited to, one or more one aluminum-salt adjuvants, one or more buffers containing one or more one volatile salts, one or more immunologically-related agents, one or more smoothing excipients, and co-stimulatory agents (e.g., co-immunostimulatory agents). In other embodiments, an immunogenic agent-containing composition disclosed herein can include some or all of: immunogenic agents such as pathogenic agents, for example, antigens, glass-forming agents, one or more adjuvants, a buffer, immunologically-related agents, and co-stimulatory agents for dehydrating in order to create immunogenic agent-containing glassy microparticles of use in fabricating the coated immunogenic agent-containing particles described herein. In some embodiments, formulations disclosed herein can be dehydrated, for example, by lyophilization, vacuum-drying, spray drying, or spray-freeze-drying or other system for dehydrating a sample.

In some embodiments, aluminum salts of use to generate an immunogenic agent-containing glassy microparticle can include one or more of aluminum hydroxide, aluminum phosphate and aluminum sulfate, or combinations thereof. In accordance with these embodiments, the aluminum salt can be in the form of an aluminum hydroxide gel (e.g., Alhydrogel®).

In some embodiments, buffers of use herein can include, but are not limited to, acetate, succinate, citrate, prolamine, histidine, borate, carbonate or phosphate buffer, or a combination thereof. In certain embodiments, a buffer can include one or more volatile salts of use in forming an immunogenic agent-containing glassy microparticle can include, but is not limited to, one or more of acetate, sodium succinate, potassium succinate, citrate, prolamine, arginine, glycine, histidine, borate, sodium phosphate, potassium phosphate, ammonium acetate, ammonium formate, ammonium carbonate, ammonium bicarbonate, triethylammonium acetate, triethylammonium formate, triethylammonium carbonate, trimethylamine acetate trimethylamine formate, trimethylamine carbonate, pyridinal acetate and pyridinal formate, or combinations thereof. In certain embodiments, the buffer can include histidine, for example, histidine-HCl.

In some embodiments, glass-forming agents of use herein can include one or more of trehalose, sucrose, ficoll, dextran, sucrose, maltotriose, lactose, mannitol, hydroxyethyl starch, glycine, cyclodextrin, and povidone, or combinations thereof. In certain embodiments, the glass-forming agent can be trehalose. In other embodiment, the trehalose concentration can be present in a weight-to-volume (w/v) concentration from about 0.1% to about 40% in an immunogenic composition prior to dehydration; from about 1% to about 30% w/v; from about 5% to about 20%; or from about 8% to about 15% w/v in the immunogenic composition prior to dehydration. In another embodiment, the glass-forming agent can be trehalose in a concentration from about 8% to about 11%; or about 9.5% w/v in the immunogenic composition prior to dehydration.

In certain embodiments, a smoothing excipient of use in compositions and methods disclosed herein can be included in the immunogenic composition to be lyophilized. In accordance with compositions disclosed herein, the smoothing excipient can aide in creation of a smooth(er) immunogenic agent-containing glassy microparticle surface, which in turn can create improved ability to deposit one or more covering layers on the immunogenic agent-containing glassy microparticle. In accordance with these embodiments, having a smooth(er) immunogenic agent-containing glassy microparticle with reduced inconsistencies on the surface reduces the risk of cracking. In certain embodiments, coating layers described herein—each of which can be about 0.1 nm or thicker—can crack or incompletely cover the immunogenic agent-containing glassy microparticle due to inconsistencies occurring on the surface of the underlying immunogenic agent-containing glassy microparticle creating raised or indented surfaces. In certain embodiments, the smoothing excipient may also function as a glass-forming agent. In some embodiments, the smoothing excipient can be hydroxyethyl starch or another pharmacologically acceptable plasma expander including, but not limited to, serum albumin, human serum albumin, dextran, hetastarch, and plasma protein factor, or the like or a combination thereof.

In other embodiments, the smoothing excipient can be hydroxyethyl starch. In some embodiments, the smoothing excipient can be present in a weight-to-volume (w/v) concentration from about 0.1% to about 40% in an immunogenic composition prior to dehydration. In other embodiments, the smoothing excipient is different from the glass-forming agent, and its concentration is from about 0.1% to about 20%. In some embodiments when the smoothing excipient is different from the glass-forming agent, the smoothing excipient concentration is from about 0.1% to about 5%; about 0.1% to about 2.5%; about 0.1% to about 1.0%, about 0.1% to about 0.5%, or about 0.1% to about 0.25% in an immunogenic composition prior to dehydration. In other embodiments, where the smoothing excipient also functions as the glass-forming agent, the smoothing excipient is present in a weight-to-volume (w/v) concentration from about 0.1% to about 40% in an immunogenic composition prior to dehydration. In some embodiments where the smoothing excipient functions as the glass-forming agent, the smoothing excipient can be in a concentration from about 1.0% to about 30% w/v, about 5.0% to about 20% (w/v), or about 8% to about 15% (w/v) in the immunogenic composition prior to dehydration.

In some embodiments, a smoothing excipient can elevate the glass transition temperatures of the immunogenic agent-containing glassy microparticles disclosed herein to further improve thermostability of the immunogenic agent-containing glassy microparticle (See, e.g., U.S. Pat. No. 7,449,444, incorporated herein by reference in its entirety).

In certain embodiments, compositions disclosed herein can include a co-stimulatory agent in order to boost immune responses to an immunogenic agent against a pathogen. In accordance with these embodiments, a co-immunostimulatory agent can include, but is not limited to, one or more of lipid A, lipid A derivatives, monophosphoryl lipid A, chemical analogues of monophosphoryl Lipid A, CpG containing oligonucleotides, TLR-4 agonists, flagellin, flagellins derived from gram negative bacteria, TLR-5 agonists, fragments of flagellins capable of binding to TLR-5 receptors, saponins, analogues of saponins, QS-21, purified saponin fractions, ISCOMS and saponin combinations with sterols and lipids, or combinations thereof.

It is understood in the art that as complexity of a vaccine or immunogenic composition increases, long term stability of the antigenic agents typically decreases, for example, when temperatures are elevated such as during storage or transport. In certain embodiments, immunogenic compositions having multiple subunits (e.g., multimeric) can be more complex than immunogenic compositions of single proteins can be less stable. For example, immunogenic compositions having antigens based on multiple capsomere subunit types can be less stable immunogenic compositions than a single subunit type. In certain embodiments, embedding a multimeric unit immunogenic compositions (e.g. capsomere) within glassy matrices formed during dehydration (e.g., by lyophilization, vacuum-drying spray-drying, or spray-freeze-drying) can enhance or increase thermal stability of the multimeric complex by, for example, by stabilizing tertiary structure of the multimeric unit(see, e.g., FIGS. 1A-1C; see also, e.g., International Patent Application PCT/US2015/036753, which is hereby incorporated by reference in its entirety). Embodiments described herein can include methods and compositions for use in stabilizing any complex pathogenic construct for use in an immunogenic composition, including, but not limited to, recombinant peptide or protein immunogens, and inactivated or attenuated pathogens.

In certain embodiments, immunogenic agents used in the thermostable immunogenic agent-containing glassy microparticles of the present disclosure can be of use for prophylactic and/or therapeutic immunogenic compositions. Suitability of immunogenic agents for use in immunogenic agent-containing particles can be tested by reaction with antibodies or monoclonal antibodies which react or recognize conformational epitopes present on the intact target of the immunogenic agent and based on the immunogenic agent's ability to elicit the production of neutralizing antiserum. Suitable assays for determining whether neutralizing antibodies are produced are known to those of skill in the art. In this manner, in certain embodiments, it can be verified whether the immunogenic agents of the present disclosure will elicit production of neutralizing antibodies.

In certain embodiments, immunogenic agents stabilized in glassy microparticles can be coated or sequestered in one or more coating layers. Certain embodiments concern using molecular deposition processes, in methods, compositions, and formulations for generating single-administration, multi-dose, thermostable immunogenic compositions. In some embodiments, immunogenic agent-containing particles can be generated where the coating or sequestering layers not only serve as adjuvants to induce an immune response, but also provide for temporally-separated primer and booster vaccine doses in a single administration to a subject. In some embodiments, immunogenic agent thermostabilization can be achieved by a combination of embedding one or more immunogenic agents in glassy organic matrices to form one or more immunogenic agent-containing glassy microparticles, and by using molecular deposition processes that enable a wide variety of molecular layers to be applied to the one or more immunogenic agent-containing glassy microparticles and encasing the one or more immunogenic agent-containing glassy microparticles to obtain encased immunogenic agent-containing glassy microparticles. In accordance with these embodiments, the thickness of these coating or sequestering layers can be controlled to within 1 or 2 angstroms in thickness, and can range from about 0.1 nm to about 20.0 nm per layer. In accordance with these embodiments, one or more coating layers can be deposited consecutively upon one another. In certain embodiments, the thickness of these coating or sequestering layers can be from about 5.0 nm to about 25.0 nm. Using a series of alternating, self-limiting surface reactions (See, e.g., FIGS. 3A-3C and FIG. 4), these coating layer deposition processes are highly scalable. For example, fluidized bed reactors can be used to allow large bulk quantities of immunogenic agent-containing glassy microparticles to be coated with coating layers without agglomeration of the particles. This process allows for complete encasement of the one or more immunogenic agent-containing glassy microparticles and can protect the one or more immunogenic agent-containing glassy microparticles from immediate deposition when administered to a subject.

In some embodiments, molecular deposition techniques can be used to apply nanometer-thick coatings of inorganic, organic, or metallo-organic materials on the surface of immunogenic agent-containing glassy microparticles. In certain embodiments, the coating or sequestering layer can be an aluminum-based material including, for example, an aluminum oxide or an aluminum alkoxide (e.g., alucone). In accordance with these embodiments, the aluminum-containing material is deposited on or applied to the surface of the one or more immunogenic agent-containing glassy microparticles to coat or sequester the one or more immunogenic agent-containing glassy microparticles in 1, 2, 3, 4, 5, 6, 7, 8, 9, 10, 11 or more layers of the aluminum-containing material to form encased immunogenic agent-containing glassy microparticles.

Figure 3A:
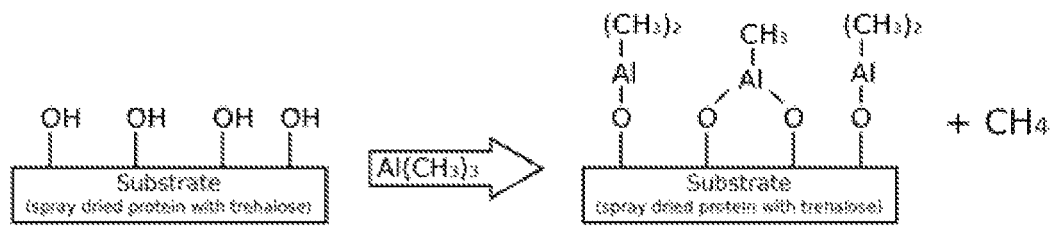
FIGS. 3A-3C are schematic diagrams that illustrate an ABC-type self-limiting reaction useful for depositing, via atomic layer deposition, thin layers of alucone as an outer layer on immunogenic agent-containing glassy microparticles according to one embodiment of the present disclosure.
Figure 3B:
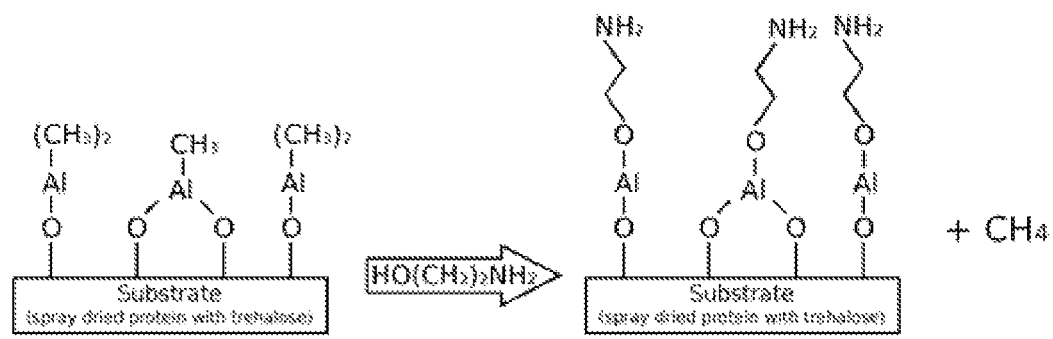
Figure 3C:
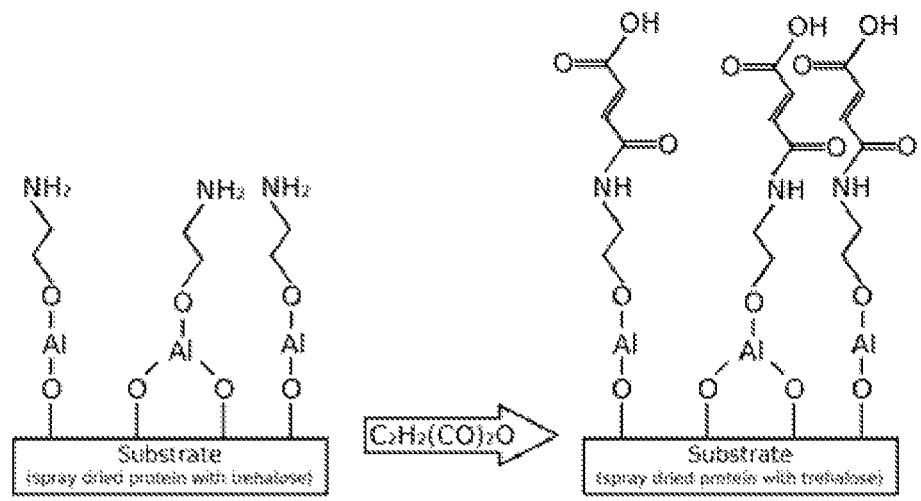

In some embodiments, aluminum-based coating layers can be used as a coating applied to particles having at least one immunogenic agent and at least one glass-forming agent (immunogenic agent-containing glassy microparticles). As illustrated in FIGS. 3A-3C, one or more layers of an aluminum-based film (coating) can be formed by coupling trimethyl aluminum to hydroxyl groups of the immunogenic agent-containing glassy microparticles (FIG. 3A), a layer of amine groups can be formed by coupling ethanolamine to the layer of aluminum-containing material (FIG. 3B), and a second layer of hydroxyl groups can be formed by coupling maleic anhydride to the available amine groups (FIG. 3C). An ABC-type reaction, for example, as illustrated in FIGS. 3A-3C can be self-limiting, and can be used to deposit molecular layers of alucone. The hydroxyl groups on the substrate (e.g., immunogenic agent-containing glassy microparticles) react with trimethyl aluminum, ethanolamine then reacts, leaving terminal amine groups on the surface, and available maleic anhydride reacts with terminal amine groups, regenerating a surface of hydroxyl groups. This ABC-type molecular deposition process can be repeated to provide additional layers as desired (See, e.g., FIG. 7), and can be used to deliver, for example, 1, 2, 3, 4, 5 or 6 doses of an immunogenic agent against a pathogen to a subject in a single administration depending on the composition or make-up of the coated or sequestered one or more immunogenic agent-containing glassy microparticles. In other embodiments, various chemical substitutes can be used in these coating or sequestering processes (e.g., alternative sources for the aluminum, amine, and/or hydroxyl groups), as would be recognized by one of ordinary skill in the art and based on the present disclosure.

Figure 4:
FIG. 4 is a schematic diagram that illustrates a binary reaction sequence for depositing, via atomic layer deposition, thin layers of alumina as an outer layer on immunogenic agent-containing glassy microparticles according to one embodiment of the present disclosure.
Figure 4:
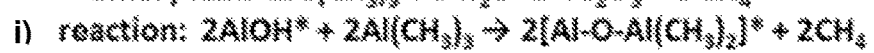
Figure 4:
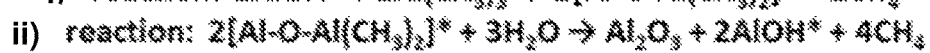
Figure 4:
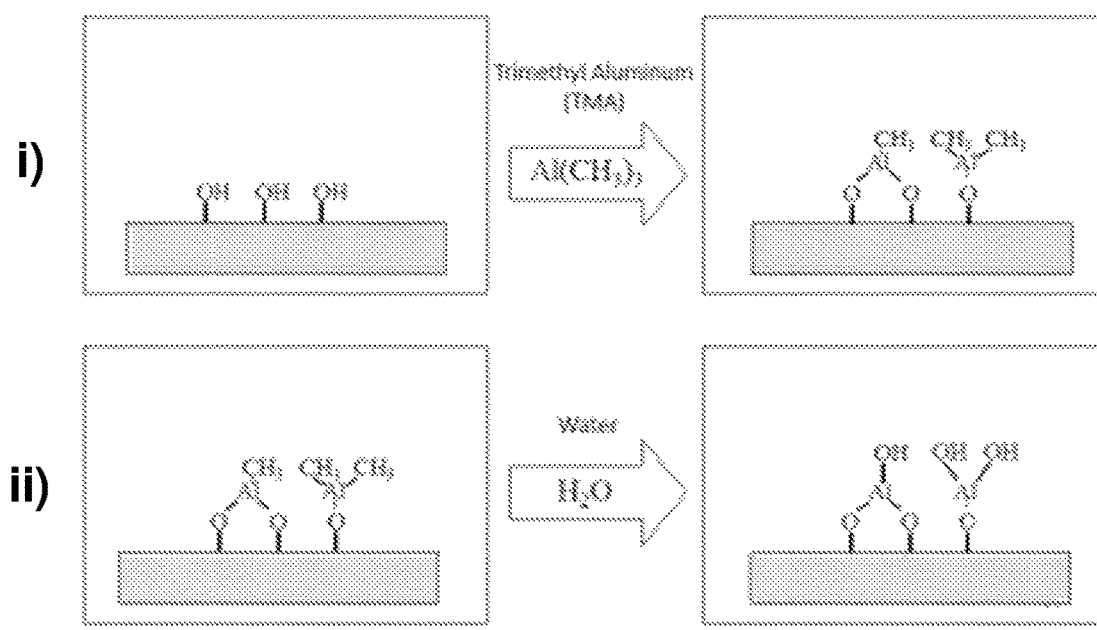

In certain embodiments, a binary reaction sequence can be used to deposit one or more layers of alumina on an immunogenic agent-containing glassy microparticle (See, e.g. FIG. 4). Immunogenic agent-containing glassy microparticles can be treated with alternating gas streams containing either trimethyl aluminum or water vapor. In certain embodiments, the number of cycles can be varied to control formation of the coating or sequestering layer on the one or more immunogenic agent-containing glassy microparticles.

In accordance with these embodiments, some advantages of depositing one or more coating layers on immunogenic agent-containing glassy microparticles include, but are not limited to, the coating layers can dissolve slowly or at a pre-determined rate when the immunogenic agent-containing particles are administered to a subject, thus allowing temporal control of the release of the particle contents (e.g., the one or more immunogenic agents). Release times can be tailored by adjusting composition(s) of the coating layers and number and/or thickness of molecular layers applied to the immunogenic agent-containing glassy microparticles. In some embodiments, about 5 to about 100 or more coating or sequestering layers can be used to form the coated or sequestered immunogenic agent-containing particles of the present disclosure. In some embodiments, release of the immunogenic agents from the coated or sequestered immunogenic agent-containing particle's core can occur within hours, to about 1 day, or about 7 days or about 30 days or about 60 days or about 90 days or about 120 days after administration to the subject. In some embodiments, release of the coated or sequestered immunogenic agents from the particle can occur from about 10 days to about 90 days after administration to the subject. In other embodiments, release of the one or more innermost sequestered or coated immunogenic agents from the particle can occur from about 30 days to about 90 days after administration to the subject. In some embodiments, release of the innermost immunogenic agents can occur from about 30 days to about 120 days, or about 30 days to about 90 days, or about 30 days to about 90 days, or about 30 days to about 60 days, after administration to the subject. In some embodiments, release of the innermost immunogenic agents can occur from about 10 days to about 21 days after administration to the subject. In some embodiments, release of the innermost immunogenic agents can occur from about 14 days to about 21 days after administration to the subject. Further, in some embodiments, release of the innermost immunogenic agents can occur from about 18 days to about 21 days after administration to the subject.

In certain embodiments, particle size of the encased one or more immunogenic agent-containing particles is from about 1 µm to about 5 µm. In other embodiments, an encased immunogenic agent-containing particle having multiple layers is less than about 5 µm in size. It will be recognized that the elements of the immunogenic agent-containing glassy microparticles, coating layers, and any additional layers can be provided in concentrations capable of providing a suitable dose of the immunogenic agent while maintaining an appropriate particle size.

Figure 7:
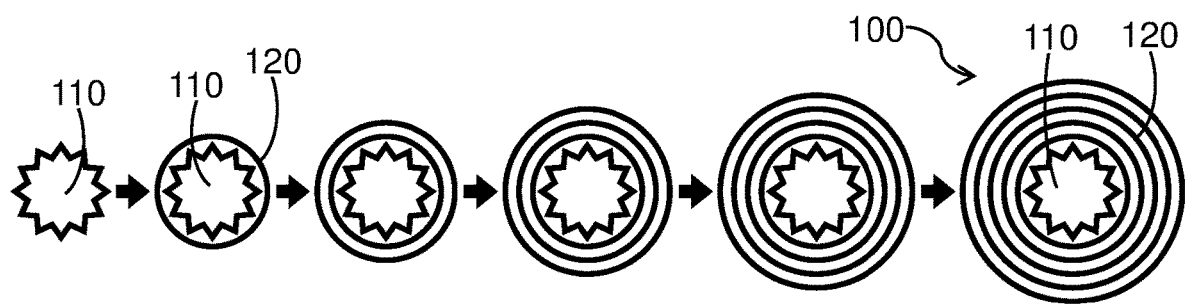
FIG. 7 is a schematic diagram illustrating deposition of coating layers on a central immunogenic agent-containing glassy microparticle to form an immunogenic agent-containing particle according to one embodiment of the present disclosure.

In certain embodiments, encased particles of the present invention can be as schematically illustrated in FIG. 7 illustrates a schematic of a coated or sequestered immunogenic agent-containing particle 100 and illustrates the addition of successive coating layers 120 on an immunogenic-agent containing glassy microparticle 110. As illustrated, multiple coating layers can be deposited on the immunogenic agent-containing glassy microparticle 110 for example, to control the dissolution rate of the coating layers 120, thus controlling the temporal release of the immunogenic agent coated within 110. The immunogenic agent-containing glassy microparticle 110 of the immunogenic agent-containing particle 100 may include one or more immunogenic agents.

In certain embodiments, one advantage of using one or more aluminum-based materials as coating or sequestering layer(s) is that the aluminum-based materials can also act as an adjuvant. In accordance with these embodiments, the aluminum-based coating layers sequestering or surrounding the immunogenic agent-containing glassy microparticles expose essentially the same surface chemistries to immunoactive cells as do standard aluminum-based adjuvant particles known in the art. In some aspects, nanoscopic aluminum-based coating layers layered on immunogenic agent-containing glassy microparticles disclosed herein can be significantly thinner than what is found in particles of conventional vaccines; therefore, total amounts of aluminum per administration will be essentially negligible, enhancing safety and reduced side effects of these agents. In certain embodiments, the aluminum-based coating layer can be sufficiently thin so that the total aluminum concentration per administration of the immunogenic composition to a subject is less than about 100 µg, less than about 20 µg, less than about 10 µg, less than about 5 µg, or less than about 1 µg or even less.

In some embodiments, coating layers other than aluminum-based coating layers can be used in order to coat or sequester the immunogenic agent containing glassy microparticles. In accordance with these embodiments, non-aluminum coating layers including, but not limited to, silicon dioxide ($SiO_2$), titanium dioxide ($TiO_2$), or silicon nitride ($Si_3N_4$) can be used either in combination with aluminum-based coating layers, or alone to the exclusion of aluminum-based coating layers. With each type of material having different characteristic dissolution times, layers of different materials can be deposited on the immunogenic agent-containing glassy microparticles to vary the temporal release of the immunogenic agent from the immunogenic agent-containing particles' core. In some embodiments, an immunogenic agent-containing glassy microparticle can be coated with one or more aluminum-based layers, followed by one or more layers of a different material. In accordance with these embodiments, different materials may dissolve more slowly than the aluminum-based coating layer. Using other materials for coating the particles, can reduce the number of aluminum-based layers necessary to provide for a given release time, minimizing the amount of aluminum per dose.

Figure 15:
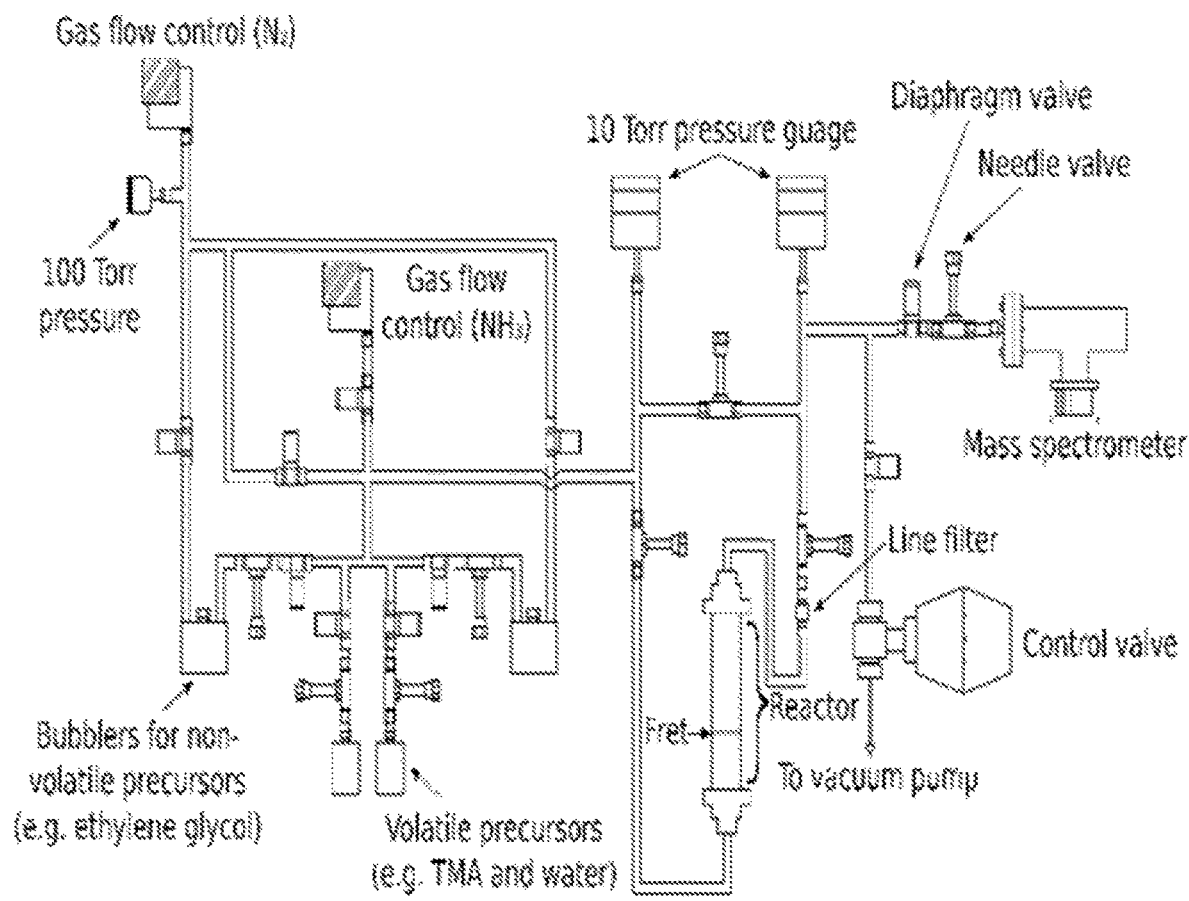
FIG. 15 is a schematic illustrating a reactor useful for coating immunogenic agent-containing glassy microparticles via atomic layer deposition (ALD) of an embodiment disclosed herein.

In other embodiments, one or more coating layers can be deposited on an immunogenic-agent containing glassy microparticle by, for example, atomic layer deposition (ALD, for example any instrumentation capable of atomic layer deposition can be used). ALD includes a thin film deposition technique that is based on the sequential use of a gas phase chemical process. ALD is considered a type of chemical vapor deposition. In certain methods, the majority of ALD reactions use two chemicals, referred to as precursors. These precursors react with the surface of a material one at a time in a sequential, self-limiting or directed manner. Through the repeated exposure to separate precursors, a thin film can be slowly deposited. Use of ALD to deposit coating layers on immunogenic agent-containing glassy microparticles can be based on sequential, self-limiting reactions (see, e.g., FIGS. 3A-3C and FIG. 4) and provides for layer thickness control at the Angstrom level and tunable coating layer composition. FIG. 15 illustrates an example of a reactor useful for coating immunogenic agent-containing glassy microparticles described herein. Examples of ALD procedures of use in methods disclosed herein for depositing coating or sequestering layers on immunogenic agent-containing glassy microparticles can be found for example in LF Hakim et al, Adv Funct Mater, 2007 November; 17 (16):3175-81, D M King et al., Powder Technol, 2012 May; 221:13-25, and X Liang et al., ACS Appl Mater Interfaces, 2009 September (web);1(9):1988-95, each of which is hereby incorporated by reference in their entirety.

In certain embodiment, the ALD method can be optimized for a particular situation or condition. For example, antigens against a pathogenic organism incorporated into immunogenic agent-containing glassy microparticles can have variable thermostability, and therefore might not be amenable to higher ALD temperatures due to this vulnerability. In certain embodiments, molecular deposition can occur at temperatures at which the at least one immunogenic agent of the immunogenic agent-containing glassy microparticle remains stable. In some embodiments, molecular deposition can occur under vacuum conditions. By performing the molecular deposition under vacuum conditions, coating layers can be applied at reduced temperatures thereby reducing adverse effects of higher temperatures on target immunogenic agents. In certain embodiments, the vacuum conditions required for deposition may be minimal. In some embodiments, the ALD process can occur under a mild vacuum of about 0.1 atmospheres. In other embodiments, ALD can also include incorporation of magnetically-coupled powder mixing devices that can lead to shorter cycle times for deposition of the material by providing uniform distribution of powders and reactants within an ALD reactor.

Embodiments of the present disclosure provide for thermostable immunogenic agent-containing particles and thermostable immunogenic compositions, where the thermostable immunogenic composition can be produced by formulating the immunogenic agent-containing particles into an immunogenic composition. In certain embodiments, these immunogenic compositions can be used as vaccines.

In one aspect, a single administration immunogenic composition can be generated and can include thermostable immunogenic agent-containing particles that provide both a prime and boost dose of one or more immunogenic agents against a pathogen. In some embodiments, prime and boost doses can be included in the same immunogenic agent-containing particle. In other embodiments, prime and boost doses can be included in separate immunogenic agent-containing particles. In accordance with these embodiment, whether together or separate, the prime and boost doses are encased in coating layers for delivery to a subject. In certain embodiments, the priming and boost dose of an immunogenic agent can form the core of an immunogenic agent-containing particle or the priming and boost dose of an immunogenic agent can form separate layers of an immunogenic agent-containing particles each layer encased by one or more layers of coating or sequestering materials.

In some embodiments, at least a second outer layer having at least a second immunogenic agent (e.g. in an aqueous or gelatinous solution) can be adsorbed to or layered on top of the outermost coating layer surrounding the immunogenic agent-containing glassy microparticles that include a first immunogenic agent. In certain embodiments, the immunogenic agent-containing glassy microparticles can be suspended in a solution of a second glass forming agent and a second antigen, and optionally a smoothing excipient, and then freeze-dried or spray dried to produce immunogenic agent-containing particles including an innermost or central first antigen and an outer second antigen. In certain embodiments, the first and second immunogenic agents and the first and second glass-forming agents can be the same or can be different agents.

Figure 8:
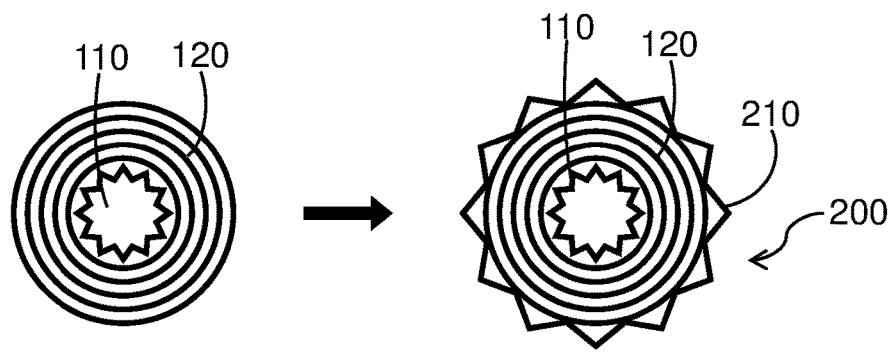
FIG. 8 is a schematic diagram illustrating formation of a second layer of immunogenic agent on the outermost coating layer according to one embodiment of the present disclosure, where the immunogenic agent of the second layer is the same as the central immunogenic agent-containing glassy microparticle.

Regarding the embodiments described herein, FIG. 8 illustrates the adsorption or adherence of a second immunogenic agent 210 to the outer-most coating layer of the particle, where the second immunogenic agent 210 on the outer layer is the same as that found in the central immunogenic agent-containing glassy microparticle. In this example, the entire particle can then be embedded in an organic glassy matrix in order to stabilize the second, outer layer of immunogenic agent. The result is a prime-boost immunogenic agent-containing particle 200. In such a configuration, the single immunogenic agent-containing particle 200 provides both prime and boost doses of the immunogenic agent in a single administration. Alternatively, the prime and boost doses can be included in separate particles, where the priming dose can be included in either an immunogenic agent-containing glassy microparticle 100 (no coating layers) or an immunogenic agent-containing particle 100 (one or more coating layers), and the boost dose is included in another immunogenic agent-containing particle 100 (see, e.g., FIGS. 12-13).

Figure 9:
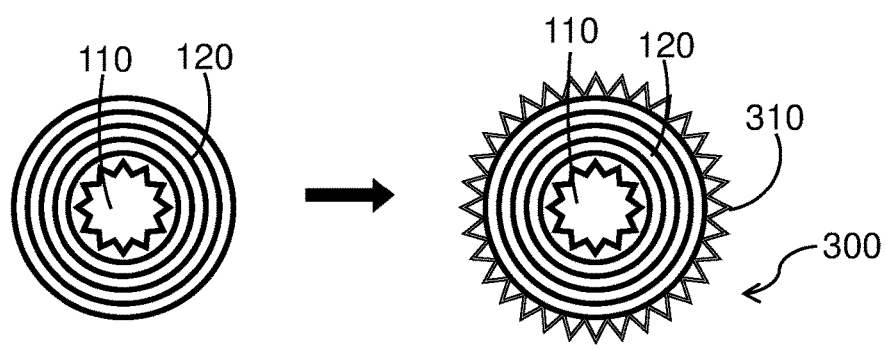
FIG. 9 is a schematic diagram illustrating formation of a second layer of immunogenic agent on the outermost coating layer according to one embodiment of the present disclosure, where the immunogenic agent of the second layer differs from the central immunogenic agent-containing glassy microparticle.

In other embodiment, FIG. 9 illustrates the adsorption of a second immunogenic agent 310 to the outer-most coating layer of the particle, where the second immunogenic agent is different from that found in the central immunogenic agent-containing glassy microparticle. The entire immunogenic agent-containing particle can then be embedded in an organic glassy matrix in order to stabilize the second, outer layer of immunogenic agent. These processes lead to a two-agent immunogenic agent-containing particle 300. The two-agent immunogenic agent-containing particle 300 provides a single dose of two distinct immunogenic agents or combinations of immunogenic agents.

Figure 10:
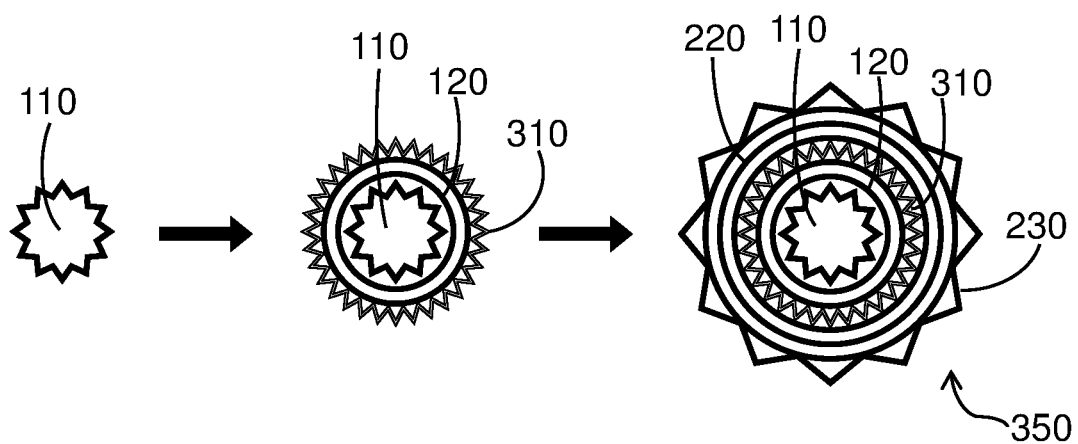
FIG. 10 is a schematic diagram illustrating formation of a dual-immunogenic agent-containing particle according to one embodiment of the present disclosure, where a layer of immunogenic agent different from that of the central immunogenic agent-containing glassy microparticle is deposited on an intermediate coating layer, followed by the deposition of a layer of immunogenic agent identical to that of the central immunogenic agent-containing glassy microparticle on the outer-most coating layer.

In yet other embodiments, FIG. 10 illustrates the formation of a relatively small number of coating layers 120, upon which a second immunogenic agent 310 that differs from the immunogenic agent of the central immunogenic agent-containing glassy microparticle is deposited. The second layer of immunogenic agent can be embedded in an glassy matrix (e.g. organic), additional coating layers 220 can be deposited on the particle. A third layer of immunogenic agent 230 can be adsorbed to the outer most coating layer to form a complex immunogenic agent-containing particle 350. As depicted in FIG. 10, the third layer 230 of complex immunogenic agent-containing particle 350 can include the same immunogenic agent as that found in the central immunogenic agent-containing glassy microparticle 110, although the third layer can include the same immunogenic agent as the second layer, or a different immunogenic agent altogether. The entire complex immunogenic agent-containing particle 350 can be embedded in an organic glassy matrix in order to stabilize the third, outermost layer of immunogenic agent-containing particle.

In certain embodiments, multi-layered immunogenic agent-containing particles disclosed herein can be reconstituted with water or an aqueous buffer composition or other pharmaceutically acceptable solution, for example, to form an immunogenic composition or formulation and subsequently administered to a subject. In one embodiment, an outer, second layer having at least a second immunogenic agent can act as a conventional priming dose. Subsequently, after a predetermined number days (the number of days can be adjusted by manipulating numbers and/or thicknesses of the coating layers applied), a sufficient amount of the coating dissolves or degrades, allowing release of a second dose (e.g. boost) from the particle core that serves to boost or supplement the priming dose response in the subject.

In other embodiments, priming (e.g. a first antigen) and boost doses of immunogenic agents to a pathogen can be included in separate immunogenic agent-containing particles. In accordance with these embodiments, the priming dose of the immunogenic agent can be included in a first thermostable immunogenic agent-containing particle (coated with one or more coating layers), or an immunogenic agent-containing glassy microparticle (no coating). The boost dose of the immunogenic agent can be included in a second thermostable immunogenic agent-containing particle coated with one or more coating layers as described herein.

Figure 11:
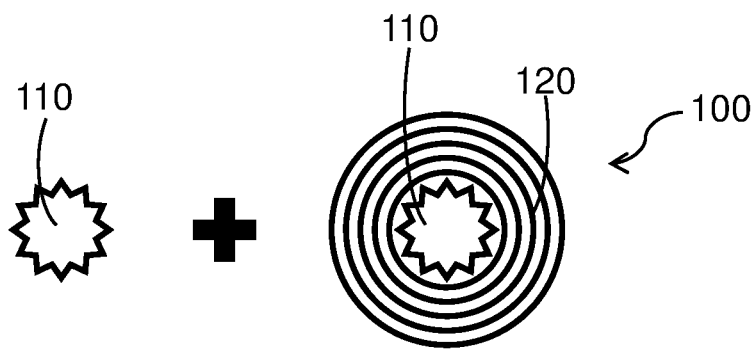
FIG. 11 is a schematic illustrating an immunogenic composition according to one embodiment of the present disclosure, where the immunogenic composition includes a prime dose in an immunogenic agent-containing glassy microparticle (no coating layers) and a boost dose in a temporally controlled immunogenic agent-containing particle (multiple coating layers).

In other embodiments, as illustrated in FIG. 11, immunogenic agent-containing particles for inclusion in a prime-boost immunogenic composition where the priming dose of the immunogenic agent is included in an immunogenic agent-containing glassy microparticle 110 and the boost dose of the immunogenic agent is included in a separate immunogenic agent-containing particle 100 where these two components can be administered to a subject in a single administration when mixed together. In certain embodiments, the two separate particles can be stored together in their dehydrated form. In other embodiments, a mixture of these immunogenic compositions can be reconstituted into a single-administration immunogenic composition. In other embodiments, the two separate particles can be stored separately, and combined prior to reconstitution. When administered to a subject, the boost dose of the immunogenic agent can be exposed to the subject at a predetermined time following the priming dose, when the coating layers have sufficiently dissolved from the boost-containing particle 100.

In certain embodiments, compositions disclosed herein can be used to administer to a subject an active agent on a predetermined schedule, such as human papilloma virus (HPV) immunogenic compositions or vaccines, where the immunogenic composition is capable of delivering multiple doses of the active agent on a predetermined schedule to the subject by dissolution of the layering on a particle. In accordance with these embodiments, various doses can be included on a single immunogenic agent-containing particle (see, e.g., FIG. 10, but where each layer of immunogenic agent include the same antigen), or in multiple immunogenic agent-containing particles. Whether the doses are carried on a single particle or multiple particles, only a single administration may be necessary or sufficient.

Figure 12:
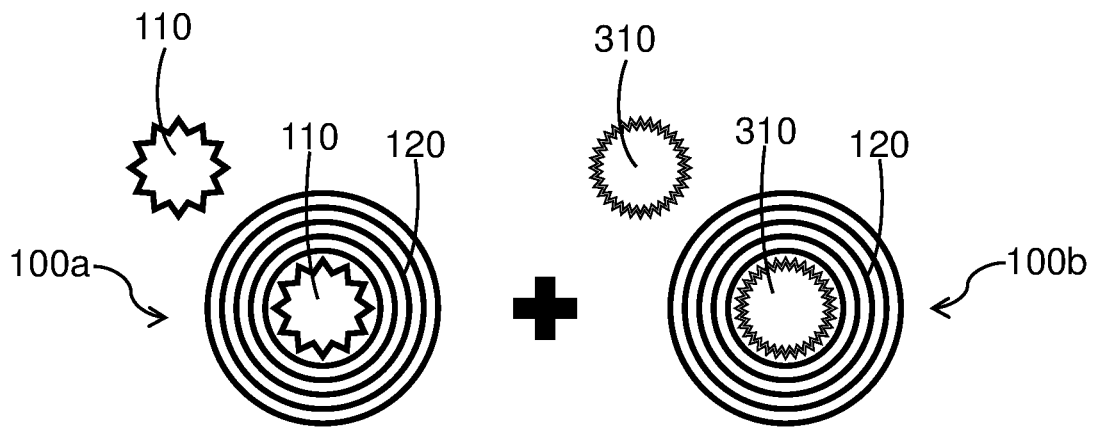
FIG. 12 is a schematic illustrating an immunogenic composition according to one embodiment of the present disclosure, where the immunogenic composition includes prime doses for two distinct targets in separate immunogenic agent-containing glassy microparticles (no coating layers) and boost doses for each target on separate temporally controlled immunogenic agent-containing particles (multiple coating layers).
Figure 13:
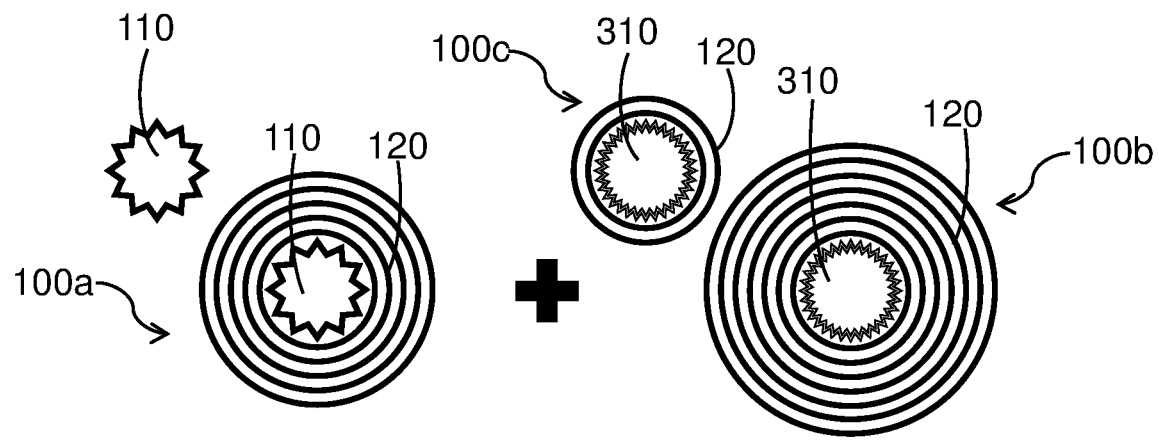
FIG. 13 is a schematic illustrating an immunogenic composition according to one embodiment of the present disclosure, where the immunogenic composition includes a prime dose to a first target in an immunogenic agent-containing glassy microparticle, a boost dose for the first target in an immunogenic agent-containing particle, a prime dose to a second target in an immunogenic agent-containing particle, and a boost dose for the second target in a separate immunogenic agent-containing particle.

In another aspect, a single-administration immunogenic agent-containing particle composition can include thermostable immunogenic agent-containing particles having immunogenic agents capable of eliciting immune responses to two or more different pathogens (See, e.g., FIGS. 10, 12 and 13). Many current vaccine compositions, such as those against infection or conditions caused by different pathogens, are incompatible when combined with one another, for example, when stored in aqueous solutions. For example, one immunogenic agent may require storage at a particular pH range, while another requires storage at a different pH range, or the immunogenic agent may require storage at different temperatures, making storage of the combined immunogenic agents unfeasible and incompatible. In other examples, immunogenic agents can create cross-reactivity or interfere with one another once administered to a subject. In some embodiments, immunogenic agent-containing particles including a first immunogenic agent can be mixed with thermostable immunogenic agent-containing particles having a second, different immunogenic agent avoiding the issues outlined above. As illustrated in FIG. 12, immunogenic agent-containing particle 100a can include immunogenic agent-containing glassy microparticle 110, while immunogenic agent-containing particle 100b can include immunogenic agent-containing glassy microparticle 310, where the immunogenic agent of immunogenic agent-containing glassy microparticle 110 is different from the immunogenic agent of immunogenic agent-containing glassy microparticle 310. The thermostable immunogenic agent-containing particles with their aluminum-based coating layers reduce incompatibilities between the two or more different immunogenic agents, whether during storage or after being administered to a subject. This reduced storage incompatibility may be due to the ability to store the immunogenic agent-containing particles separately, or even together, in a thermostable, lyophilized state.

As described herein, thermostable immunogenic agent-containing particles with their aluminum-based coating layers reduce incompatibilities between the two or more different immunogenic agents, whether during storage or after being administered to a subject. In other embodiments, immunogenic agent-containing particles can include two or more different immunogenic agents (e.g., two or more different antigens) in the same particle (See e.g. FIGS. 9 and 10). In these embodiments, the immunogenic agent-containing particles are safeguarded against incompatibilities between the two or more different immunogenic agents due to their stabilization within the glassy matrix, and in certain embodiments due to physical separation of the immunogenic agents by one or more coating layers.

In certain embodiments, immunogenic agent-containing particles having different immunogenic agents can have different thicknesses of aluminum-based coating layers to temporally control release of the immunogenic agents. By temporally controlling release of the different immunogenic agents, multiple immunogenic agents can be included in a single-administration immunogenic composition while minimizing the risk of cross-reactivity or interference between the different immunogenic agents. This can be accomplished by having each of the immunogenic agents be released at a different time point. For example, a single-administration multi-immunogenic agent formulation can include primer-boost doses of an immunogenic agent against a first pathogen, and primer-boost doses of an immunogenic agent against a second pathogen. The primer-boost doses of each of the first and second immunogenic agents can be included in one or more particles. For example, the particle including the primer dose against the first pathogen can have a small number of aluminum-based coating layers, or none at all, resulting in an early primary response to the immunogenic agent against the first pathogen when administered to a subject. A second particle including the primer dose of the second immunogenic agent can have a number of aluminum-based coating layers sufficient to delay exposure of the primer dose of immunogenic agent of the second pathogen until a sufficient primary response to the primer immunogenic agent of the first pathogen has occurred. This can minimize the risk of cross-reactivity or immune interference in a subject between the primer immunogenic agents against the first and second pathogens. An optional third particle including the boost dose for the first immunogenic agent (See e.g. FIG. 12) can have a number of aluminum-based coating layers sufficient to delay exposure of the boost dose for the first immunogenic agent for a predetermined period of time. An optional fourth particle including the boost dose for the second immunogenic agent (see, e.g. FIG. 12) can have a number of aluminum-based coating layers sufficient to delay exposure of the boost dose of the second immunogenic agent for a predetermined period of time. In accordance with these embodiments, the timing when any of the immunogenic agents of the various doses can be exposed to the subject by dissolution of the layers can be adjusted by varying the number and/or thickness of layers of aluminum-based coating layers of the particles.

In one embodiment, four immunogenic agent-containing particles are illustrated in FIG. 13. As represented in FIG. 13, the prime dose of the first immunogenic agent can be included in an immunogenic agent-containing glassy microparticle 110. The prime dose of the second immunogenic agent can be included in immunogenic agent-containing glassy microparticle 310, which is coated with a coating layer 120 to form immunogenic agent-containing particle 100c. Coating layer 120 of immunogenic agent-containing particle 100c can be sufficiently thick to allow a primary response to the first immunogenic agent of immunogenic agent-containing glassy microparticle 110, and prevent cross-reactivity or interference between the two immunogenic agents. Immunogenic agent-containing particle 100a includes the same immunogenic agent as found in glassy microparticle 110, thus providing a boost dose. The coating layer 120 of immunogenic agent-containing particle 100a can be sufficiently thick to delay release of the immunogenic agent of particle 110a. In certain embodiments, release can be delayed until a sufficient primary response to the second immunogenic agent of immunogenic agent-containing particle 100c has occurred. Immunogenic agent-containing particle 100b can include the same immunogenic agent as found in immunogenic agent-containing particle 100c, thus providing a boost dose. The coating layer 120 of immunogenic agent-containing particle 100b is sufficiently thick to delay release of the immunogenic agent of particle 110b. In certain embodiments, release may be delayed until a sufficient boost response to the first immunogenic agent of immunogenic agent-containing particle 100a has occurred.

In certain embodiments, when cross reactivity or interference between two or more immunogenic agents is not of concern, priming responses can be elicited at the same time against two or more pathogens by including immunogenic particles having similar or identical time release of the priming dose of each immunogenic agent against a particular pathogen (See e.g., FIG. 12). In certain embodiments, immunogenic agent-containing glassy microparticles (e.g., no coating layers applied to the particles) including the primary dose of each immunogenic agent can be used. The primary doses can be included in the same immunogenic agent-containing glassy microparticle, or in separate immunogenic agent-containing glassy microparticles.

In certain embodiments, single-administration immunogenic or vaccine formulations capable of eliciting immune responses to two or more different pathogens can be made by combining two or more different immunogenic agents prior to forming immunogenic agent-containing glassy microparticles by the methods described in the present disclosure. This can result in a single immunogenic agent-containing particle having immunogenic agents against two or more different pathogens. In other embodiments, single-administration immunogenic or vaccine formulations can be made by combining immunogenic agent-containing particles formed by the methods described in the present disclosure, where the immunogenic agent-containing particles include immunogenic agents for different pathogens. This can result in a mixture of immunogenic agent-containing particles, where individual particles include multiple antigens for different pathogens. In some embodiments, immunogenic agent-containing particles of a mixture can include immunogenic agent-containing particles having immunogenic agents against two or more different pathogens and other immunogenic agent-containing particles having immunogenic agents for a single pathogen.

Figure 14:
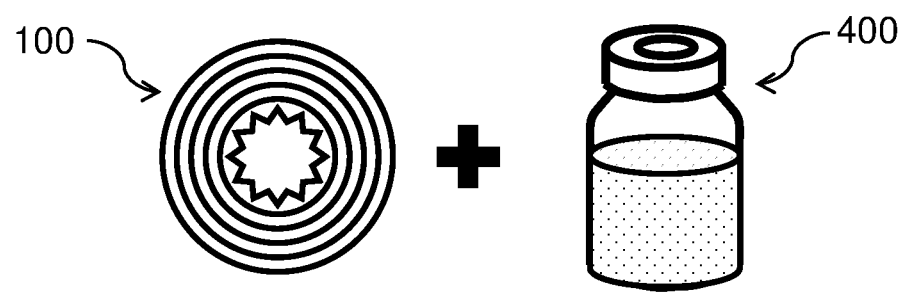
FIG. 14 is a schematic illustrating an embodiment of the present disclosure, where a boost dose in the form of immunogenic agent-containing particles is added to an existing vaccine composition to form a prime-boost single-administration immunogenic composition.

In certain embodiments, immunogenic agent-containing particles 100 of the present disclosure having one or more coating layers can be added to a common, existing immunogenic or vaccine composition 400 to create a single-administration prime-boost immunogenic composition (see, e.g., FIG. 14). Existing immunogenic formulations will can serve as a priming dose, while added immunogenic agent-containing particles of the instant disclosure can serve as a boosting dose at a predetermined time, (e.g., when the coating layer(s) sufficiently dissolve(s)). In accordance with these embodiments, this provides for a single-dose immunogenic composition from existing immunogenic or vaccine formulation stocks. Certain advantages of such a single-dose immunogenic composition can, for example, increase patient compliance and reduce overall costs as well as take advantage of current stocks of these formulations, and a single administration is required. The existing vaccine composition stocks can be made into single-dose immunogenic compositions by the addition of one or more additional doses in the form of time-released immunogenic agent-containing particles. In some embodiments, immunogenic agent-containing particles described herein can be added to known and commercially available immunogenic compositions, including commercially available immunogenic compositions, for example, those directed against measles, tetanus, diphtheria, pertussis, influenza, poliovirus, rotavirus, hepatitis B, hepatitis C, yellow fever, malaria, human papilloma virus, dengue virus, Japanese encephalitis virus, Zika virus, Ebola virus, norovirus, varicella, herpes simplex, cytomegalovirus, ricin toxin, *Bacillus anthraces*, and *Clostridium botulinum*.

Embodiments of the present disclosure can include polypeptides, proteins, virus-like particles, inactivated or attenuated pathogens (e.g. live, attenuated viruses), or other antigens that elicit an immune response when introduced to a subject. In accordance with these embodiments, an elicited immune response can be a prophylactic response, reducing or preventing infection, disease, or toxicity induced by exposure to a pathogen including, but not limited to, a virus bacteria, or fungus, or toxin, and/or can be therapeutic, reducing the severity of infection, disease or toxicity when exposed to a pathogen or toxin. An immune response can include a humoral (e.g., antibody) response to an antigen derived from or directed to a pathogen and/or a cell-mediated response to an antigen derived from or directed to a pathogen. Methods to measure or observe an immune response to a particular pathogen are known in the art (e.g. neutralization assays). If one or both types of immune response are created in a subject, they can reduce the risk of or protect the subject from onset of an infection, for example, by attacking pathogen from which the antigen was derived. In accordance with the present disclosure, the ability of a composition including immunogenic agent-containing particles to reduce infection by or protect a subject from disease refers to its ability to treat, ameliorate, reduce the risk and/or prevent disease or infection caused by the pathogen or cross reactive agent, in some aspects, by eliciting an immune response against an immunogenic agent (e.g., antigen) derived from the pathogen, or condition-causing agent found in the immunogenic agent-containing particle. It is to be noted that a subject administered an immunogenic composition disclosed herein may be protected by or have decreased risk of infection by receiving a composition disclosed herein even without detection of a humoral and/or cell-mediated response to the composition.

Protective immunity, allowing a mammal or other animal to resist (delayed onset of symptoms or reduced severity of symptoms or complete elimination of infection), can be due to exposure to the antigen of a pathogen, disease or toxin that otherwise follows contact with the pathogen. Protective immunity is achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes that result in sIGA production by B lymphocytes on mucosa-lined tissues of the body. "Humoral immunity" includes IgG antibodies and IgM antibodies in serum. "Cellular immunity" can be achieved through cytotoxic T lymphocytes or through delayed-type hypersensitivity that involves macrophages and T lymphocytes, as well as other mechanisms involving T cells without a requirement for antibodies. The primary result of protective immunity is the destruction of the pathogen or inhibition of its ability to replicate itself Certain embodiments of the present disclosure include methods to elicit an immune response to an immunogenic agent of an immunogenic agent-containing particle or combination of immunogenic agents of one or multiple immunogenic agent-containing particles, by administering to the subject a composition including immunogenic agent-containing particles disclosed herein. The immunogenic composition including the immunogenic agent-containing particles can be administered in therapeutically effective amounts. That is, in amounts sufficient to produce a protective immunological response. Generally, the immunogenic or vaccine compositions can be administered in active agent dosages ranging from about 0.001 mg to about 20.0 mg immunogenic agent or about 0.01 mg to about 20.0 mg immunogenic agent, or about 0.1 mg to about 10.0 mg immunogenic agent. Single or multiple dosages can be administered in a single administration composition. Where multiple doses of an immunogenic or vaccine composition are administered in a single administration composition, for example, in prime-boost compositions, one of the two doses can be temporally controlled for release at a pre-selected time after administration.

In certain embodiments, administration of immunogenic or vaccine compositions of the present disclosure can be performed using any acceptable means (e.g., parenterally, locally or systemically, including by way of example, oral, intranasal, intravenous, subcutaneous, intradermal, intravaginal, by suppository, intramuscular, and topical administration). In some embodiments, administration of immunogenic compositions disclosed herein can be affected by factors including a natural route of infection by a particular pathogen. Dosage or dosages administered can depend upon factors including the age, health, weight, kind of concurrent treatment, exposure, if any, and the nature and type of the particular immunogenic agent. Immunogenic compositions or vaccine composition disclosed herein can be employed in dosage form such as capsules, liquid solutions, suspensions, or elixirs, for oral administration, or sterile liquid formulations such as solutions or suspensions for parenteral or intranasal use.

Kits

Other embodiments provide kits of use with the methods (e.g., methods to elicit an immune response in a subject) and compositions described in the present disclosure. In certain embodiments, a kit may contain one more immunogenic agent-containing particles in a dehydrated form. In certain embodiments, immunogenic agent-containing glassy microparticles can also be provided. Different immunogenic agent-containing particles and/or immunogenic agent-containing glassy microparticles can be provided mixed together, or separate. In certain embodiments, different immunogenic agent-containing particles and/or immunogenic agent-containing glassy microparticles are provided mixed together. Immunogenic agent-containing particles and/or immunogenic agent-containing glassy microparticles can be provided in a known quantity and/or at a predetermined ratio so that when the particles are reconstituted, the result is an immunological composition with a known concentration of immunogenic agent.

In other embodiments, kits are contemplated of use for compositions, and methods described herein. Kits can be portable. In certain embodiments, kits can be used to transport to and be used in remote areas such as military installations or remote villages. The thermostability of the immunogenic agent-containing glassy microparticles and immunogenic agent-containing particles allows for transport and storage without the need for a cold chain (e.g., refrigeration). This can also be advantageous in healthcare facilities, as it reduces costs associated with cold storage.

In other embodiments, kits can include an appropriate carrier or diluent suitable for reconstituting the dry thermostable particles. In certain embodiments, the carrier or diluent can be a pharmaceutically acceptable aqueous buffer suitable for injection that includes pyrogen-free water and has the ability to resist changes in pH upon addition of an inorganic compound, organic compound, acid, alkali, or dilution with a solvent or diluent.

In some embodiments, kits can include one or more suitable containers, for example, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the immunogenic agent-containing agents and/or immunogenic agent-containing glassy microparticles, pharmaceutically acceptable carrier or diluent and any other reagent containers in close confinement for commercial sale. Such containers may include injection or blow-molded plastic containers into which the desired vials are retained.

In yet other embodiments, kits can include immunogenic agent-containing glassy microparticles and compositions and instructions for coating the immunogenic agent-containing glassy microparticles. In other embodiments, the kit can include an apparatus for performing such coatings on immunogenic agent-containing glassy microparticles. In accordance with these embodiments, the kits allow for production of immunogenic agent-containing particles of use in immunogenic compositions against one or more pathogens.

It will be recognized that the embodiments described herein can be applied to pharmaceutical compositions other than immunogenic compositions. For example, small molecule drugs (e.g. anti-cancer agents) and biologics may be similarly coated as disclosed for immunogenic agent-containing glassy microparticles described herein. The coating layers provide for a level of temporally controlled release desirable with certain pharmaceutical agents. The coating layers can serve to reduce exposure to moisture, reducing degradation. These coatings can function to protect water-soluble drug formulations or other moisture sensitive agents from degradation or dissolution until desired exposure to a subject after administration. Further, the embodiments may be used in applications outside of therapeutics. For example, coating layers may be applied to diagnostic markers. The coatings may allow delayed release of the marker, allowing sufficient trafficking/uptake time. This may be beneficial where the marker has a limited half-life. In certain embodiments, immunogenic compositions disclosed herein or encapsulated small molecules using layering/coating technologies described herein can be administered directly to an affected location of a subject such as the liver or kidney or brain depending on the ability of the deposited composition to remain in the targeted region.

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this invention, and without departing from the spirit and scope thereof, can make various changes and modifications of the invention to adapt it to various usages and conditions.

Example 1

Deposition of Aluminum-Based Coating Layers on Trehalose Glassy Microparticles

In certain exemplary methods, trehalose glassy microparticles including either alkaline phosphatase or fluorescein were produced (see, e.g., U.S. Pat. Nos. 8,444,991 and 8,808,710, as well as A L Clausi et al., J Pharm Sci, 2008 June; 97(6):2049-61, K J Hassett et al., Eur J Pharm Biopharm, 2013 October; 85(2):279-86, K J Hassett et al., J Pharm Sci, 2015 February; 104(2):627-39, and K J Hassett et al., Eur J Pharm Biopharm, 2015 August; 94:220-8). The trehalose microparticles were then coated with nanometer-thick aluminum alkoxide or alucone as illustrated (see, e.g., FIG. 3). It is noted that these processes depicted in FIG. 3 can be repeated depending on the desired layering on a target immunogenic agent-containing glassy microparticle.

Figure 6A:
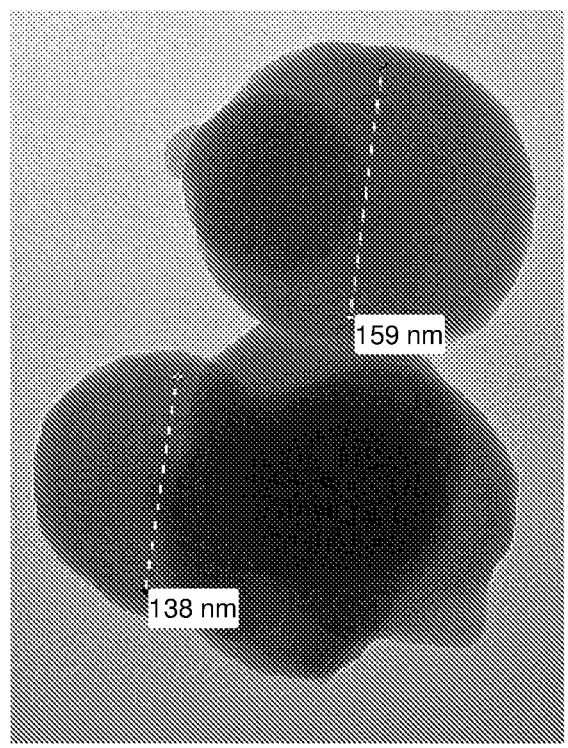
FIG. 6A is a representative photograph of alucone-coated alkaline phosphatase particles.

In certain exemplary methods, studies demonstrated that a target polypeptide, alkaline phosphatase, retained complete enzymatic activity when it was incorporated by spray-freeze-drying or spray drying into trehalose-formulated microparticles, with coating layers (e.g. alucone layers), and released into aqueous media after incubation at 37° C. (see FIGS. 6A-6B) . To test the acute stability of the enzyme during the ALD process, these preliminary studies used relatively thin layers (ca. 15 nm, built up over 100 cycles) and a testing solution at high pH (pH 9) in order to speed dissolution and allow essentially complete release of the particle contents over a 24 hour period.

To determine the release rate of an immunogenic agent from an immunogenic agent-containing glassy microparticle, trehalose glassy microparticles including fluorescein can be used. Trehalose glassy microparticles including fluorescein can be coated with varying numbers of aluminum-based coating layers. Incubating the coated particles in physiological conditions (e.g., 37° C. in phosphate buffered solution) and measuring release of fluorescein into the storage fluid will allow for the determination of release rates in particles having various numbers of layers.

Figure 1B:
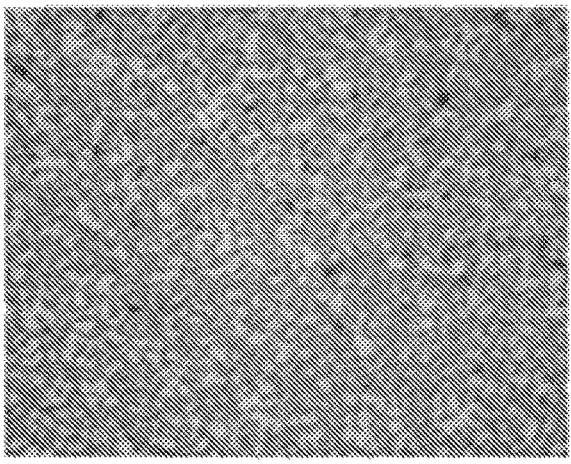
Figure 1C:
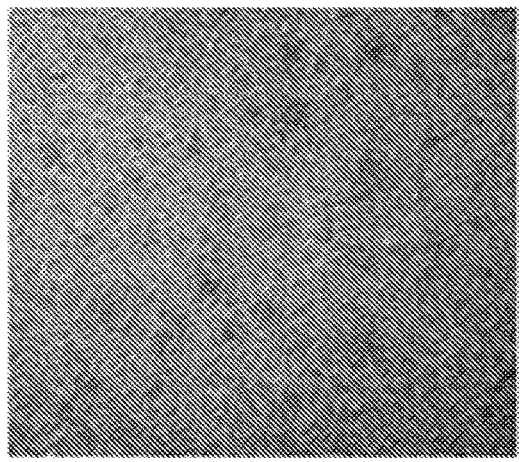

FIGS. 1A-1C are representative electron micrographs of HPV L1 capsomeres before lyophilization (A), immediately after lyophilization and reconstitution (B), and after storage in the lyophilized state and reconstituted (C), according to one embodiment of the present disclosure and of use for making immunogenic agent-containing particles disclosed herein.

Figure 2A:
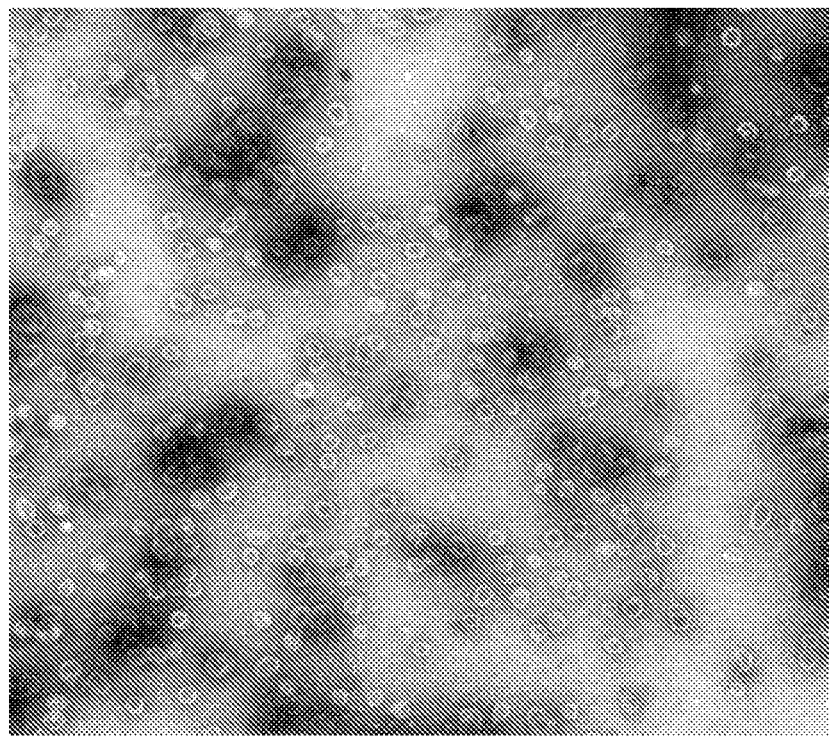
FIGS. 2A-2B are representative electron micrographs of HPV 16L1 virus-like particles (VLPs) prior to lyophilization (FIG. 2A) and following lyophilization and reconstitution (FIG. 2B). Scale bars=100 nm.
Figure 2B:
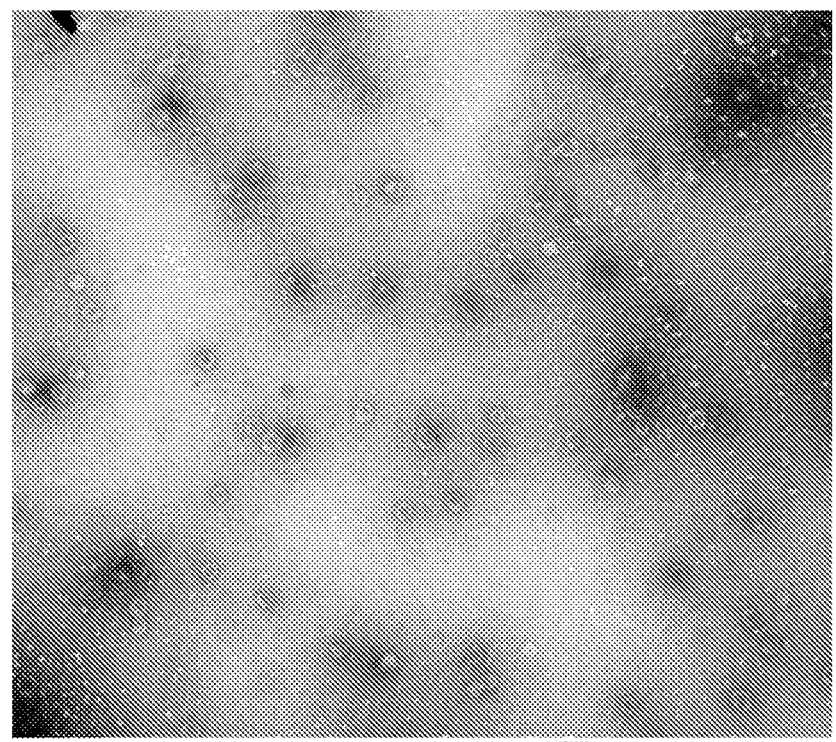

FIGS. 2A-2B are representative electron micrographs of HPV 16L1 virus-like particles (VLPs) prior to lyophilization (FIG. 2A) and following lyophilization and reconstitution (FIG. 2B) of use for making immunogenic agent-containing particles disclosed herein.

Figure 5A:
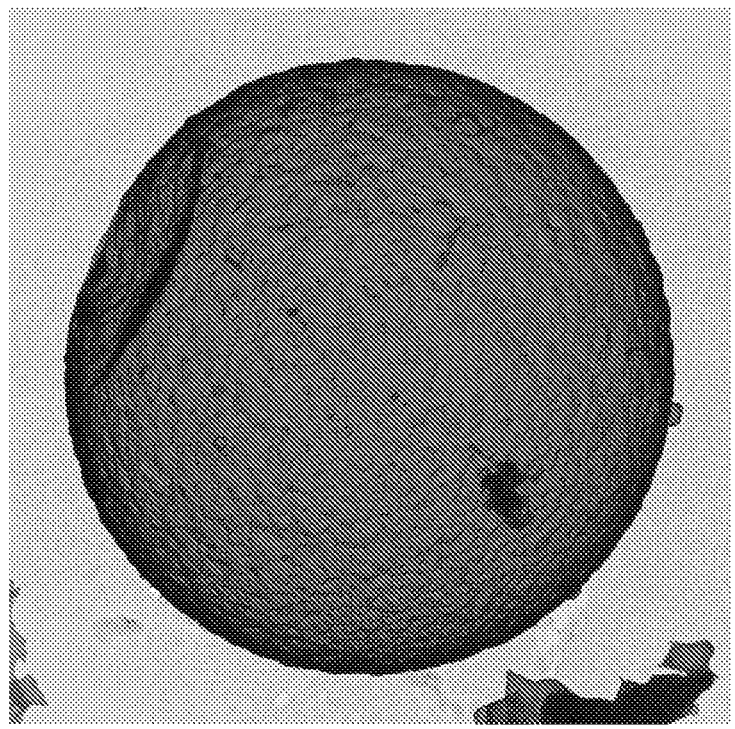
FIG. 5A is a transmission electron micrograph depicting a representative example of an intact alumina-coated particle according to one embodiment of the present disclosure.
Figure 5B:
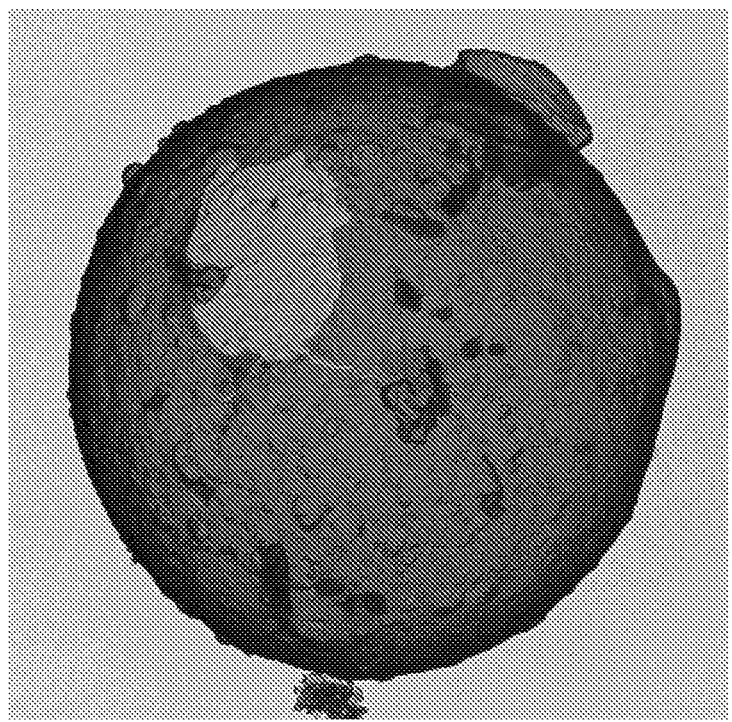
FIG. 5B is a transmission electron micrograph depicting a representative example of a ruptured alumina-coated particle, where the inner contents are exposed to the surrounding environment, according to one embodiment of the present disclosure.
Figure 6B:
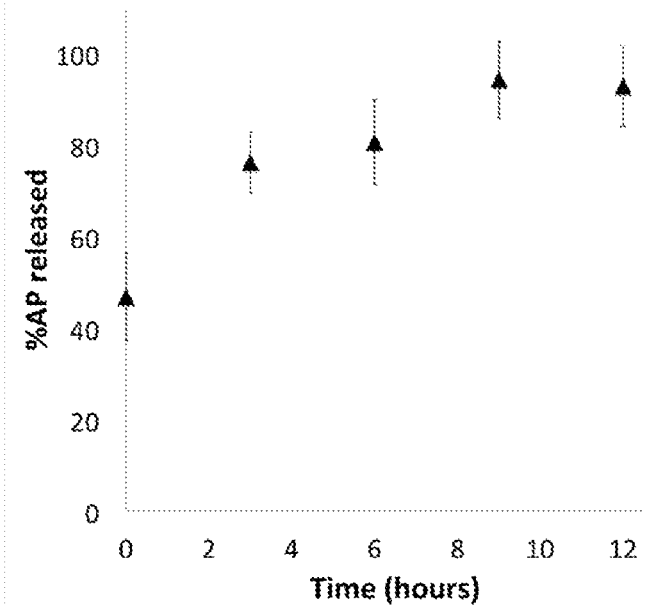
FIG. 6B illustrates the release of alkaline phosphatase from the alucone-coated alkaline phosphatase particles of FIG. 6A over time.

FIGS. 5A-5B depict transmission electron micrographs of a glassy microparticle having an intact coating layer (FIG. 5A) or a ruptured coating layer (FIG. 5B), the hole through which the content of the glassy microparticle escaped into aqueous solution. FIG. 5A is an electron micrograph depicting the coating layer of a trehalose/histidine/alkaline phosphatase/coomassie blue glassy microparticle. The glassy microparticles were created by spray-freeze drying solutions containing 15 wt % trehalose, 54 mM histidine buffer, Coomassie Blue dye (for aid in visualizing the particles) and the enzyme alkaline phosphatase. Escape of the alkaline phosphatase into aqueous solution through the ruptured covering layer is readily detectable (see, e.g., FIG. 6B and Example 1). FIG. 6B is a photograph depicting intact particles that include a glassy microparticle (trehalose and alkaline phosphatase) and a 15 nm thick coating layer of alucone. Following incubation in buffered saline, active alkaline phosphatase was released after about 8 hours (see, e.g., FIG. 6B).

Example 2

Trivalent HPV Immunogenic Agent-Containing Particles

In one exemplary method, three different pathogens can be combined using compositions and methods disclosed in the present application. In this example, 0.1 mg of HPV L1 capsomere from each of HPV 16, 18, and 31 can be combined with 9.5% (w/v) trehalose and 0.5% (w/v) hydroxyethyl starch in a buffer (e.g. 54 mM histidine (pH 7.1)) to form a primary trivalent immunogenic composition. The primary trivalent immunogenic composition can then be lyophilized. In this example, lyophilization can be by filling a 3 ml lyophilization vial with 1 ml of the primary trivalent immunogenic composition and placing the filled vial centrally on a tray freeze dryer shelf pre-cooled to about −10° C. The vial containing the primary trivalent immunogenic composition can be surrounded by 3 ml edge vials containing 1 ml water to protect the central vial from radiative heat from the walls or edge vial effects. The temperature of the freeze dryer shelf may then be lowered to about −40° C. at a rate of about 0.5° C./min, and maintained at about −40° C. for 1 hour. Following this freezing step, vacuum may be pulled to bring the chamber pressure of the freeze dryer shelf to about 60 mTorr initiate primary drying. For the remainder of the lyophilization procedure, the chamber can be kept at about 60 mTorr. Primary drying can begin with shelf temperature maintained at about −40° C. for 30 min before being raised to about −20° C. at a rate of about 1° C./min, and held for about 20 hours. To remove any remaining water, secondary drying can be initiated by increasing the shelf temperature to about 0° C. at a rate of about 0.2° C./min and then to about 30° C. at a rate of about 0.5° C./min. Shelf temperature can be held at about 30° C. for about 5 hours to complete the secondary drying step. Shelf temperature can then be returned to about 20° C. and the vials containing the primary trivalent immunogenic composition can be back-filled by bleeding nitrogen into the freeze dryer shelf chamber until atmospheric pressure is achieved. This process provides for trivalent glassy immunogenic-agent containing particles that include HPV L1 capsomeres from HPV types 16, 18, and 31 in a glassy matrix formed by the trehalose and hydroxyethyl starch. The vials containing the trivalent immunogenic agent-containing glassy microparticle can be stoppered in the freeze dryer shelf chamber and stored at about −80° C. until applying the one or more coating layers.

Once the glassy microparticles are formed, these trivalent immunogenic agent-containing glassy microparticles can be coated with layers of aluminum oxides or aluminum alkoxides using a series of alternating, self-limiting surface reactions (see, e.g. FIGS. 3 and 4) by atomic layer deposition (ALD) in a fluidized bed reactor to produce trivalent immunogenic agent-containing particles. Reactors similar to that depicted by FIG. 15 may be used in methods similar to those described by L F Hakim et al, Adv Funct Mater, 2007 November; 17 (16):3175-81, D M King et al., Powder Technol, 2012 May; 221:13-25, and X Liang et al., ACS Appl Mater Interfaces, 2009 September (web);1(9):1988-95 to coat the trivalent immunogenic agent-containing glassy microparticles.

The immunogenic agent-containing particles can then be combined with uncoated trivalent immunogenic agent-containing glassy microparticles to produce a single administration HPV prime-boost composition. The single administration HPV prime-boost composition can be reconstituted and administered to a patient (e.g. adolescent or young adult) to provide a trivalent HPV priming dose and a trivalent HPV boost dose about 1 to 2 months after the priming dose. The trivalent immunogenic agent-containing glassy microparticles can initiate a primary response in the patient, and the coating layer of the trivalent immunogenic agent-containing particle will slowly dissolve to expose the trivalent HPV boost dose.

Example 3

Tetravalent HPV Immunogenic Agent-Containing Particles

In another exemplary embodiment, HPV L1 capsomere from each of HPV 16, 18, 31, and 45 can be incorporated into tetravalent immunogenic agent-containing glassy microparticles (uncoated) and immunogenic agent-containing particles (coated) can be produced using the processes described in Example 2. If additional boosts are desired, ALD layering as described above can be used to provide additional coatings to generate HPV immunogenic agent-containing particles with more coats layered on the tri- or tetra-valent immunogenic agent-containing glassy microparticles providing exposure to the tri- or tetra-valent immunogenic agent-containing glassy microparticles about 6 months after the priming dose.

Example 4

Tetravalent Live Attenuated Dengue Virus-Containing Particles

In another exemplary method, single-administration, prime-boost tetravalent vaccines containing live attenuated viruses of each of the four serotypes of dengue virus may be prepared by first creating suspensions of each of the four serotypes (e.g. live attenuated viruses or chimeras etc.) in solutions containing 7% weight/volume of the glass-forming agent trehalose, 2% weight/volume of the smoothing agent hydroxyethyl starch, a volatile buffer such as ammonium acetate, and 100 µM polysorbate 80. These suspensions can be processed by spray-drying in order to form glassy microparticles with diameters ranging from about 2 to 5 microns. Subsequently, the glassy microparticles can be coated with layers of alumina using the ALD process disclosed herein in a fluidized bed reactor. In this ALD process, the alumina layers can be deposited on the particles by exposing the particles to a fluidizing gas stream composed of an inert carrier gas such as nitrogen and alternating concentrations of the ALD reactants water vapor or trimethyl aluminum vapor. Sufficient layers are applied so that after parenteral administration of the alumina-coated particles to a subject, the live attenuated viruses are released to provide a booster dose only after extended periods of time, e.g., 30 days to 6 months after their parenteral administration of a tetravalent formulation of dengue virus or other dengue virus vaccination. Alternatively, the alumina-coated particles (immunogenic agent-containing particles) can be co-administered parenterally to a subject (e.g. traveler) after suspending them in a solution containing the prime dose of live attenuated dengue virus.

Example 5

Equine Sarcoma Vaccine Using Alumina-Coated Glassy Microparticles Containing L1 Capsomeres of Bovine Papillomavirus In another exemplary method, a multidose, dry-powder formulation of an equine vaccine to reduce onset of or prevent sarcomas in horses resulting from infection by bovine papilloma virus can be prepared. L1 capsomeres of the bovine papilloma virus can be produced in $E.\ coli$ using standard recombinant techniques and purified by ion-exchange and size-exclusion chromatography. Purified L1capsomeres can then be suspended in a solution containing 10% weight/volume trehalose, 50 mM histidine buffer, and 100 µM polysorbate 20. Immunogenic agent-containing glassy microparticles can be prepared by spray drying the suspension in a conventional Buchii spray dryer, using gas flowrates and gas temperatures adjusted so that the exit temperature of gas from the spray dryer does not exceed 60° C. Alumina coatings can then be applied to the glassy, immunogen-containing particles as described in Example 4. The resulting dry powder can be suspended in a suitable suspending medium such as pharmaceutically acceptable isotonic saline solution (e.g. sterile solution) and placed in a syringe for single dose use or in a multi-dose delivery device for multi-dose use prior to parenteral administration to a horse or several horses.

All of the compositions and methods disclosed and claimed herein can be made and executed without undue experimentation in light of the present disclosure. While the compositions and methods have been described in terms of embodiments, it is apparent to those of skill in the art that variations maybe applied to the compositions and methods and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. An immunogenic agent-containing particle comprising:
   a central or innermost immunogenic agent-containing glassy microparticle comprising at least one immunogenic agent and at least one glass-forming agent wherein the at least one immunogenic agent is in an essentially dried glassy state; and
   one or more coating layers covering the central or innermost immunogenic agent-containing glassy microparticle, wherein each layer of the one or more coating layers comprises one or more of aluminum oxide ($Al_2O_3$), an aluminum alkoxide, silicon dioxide ($SiO_2$), titanium dioxide ($TiO_2$), and silicon nitride ($Si_3N_4$).

2. The immunogenic agent-containing particle according to claim 1, wherein the central or innermost immunogenic agent-containing glassy microparticle further comprises at least one smoothing excipient.

3. The immunogenic agent-containing particle according to claim 1, wherein the at least one immunogenic agent comprises one or more antigens from a pathogenic virus, a pathogenic bacteria, a fungal pathogen; a peptide or polypeptide derived from a pathogenic virus, a pathogenic bacteria or fungal pathogen; a recombinant molecule derived from a pathogenic virus, bacterial pathogen or fungal pathogen; an inactivated pathogenic virus, pathogenic bacteria, or fungal pathogen; a chimera or a toxoid agent.

4. The immunogenic agent-containing particle according to claim 1, wherein the at least one immunogenic agent comprises a recombinant viral protein; a virus-like particle; a live virus; a live, attenuated virus; an inactivated virus; one or more viral proteins; or a combination thereof.

5. The immunogenic agent-containing particle according to claim 1, wherein the at least one immunogenic agent comprises one or more antigens derived from human papilloma virus, Ebola virus, poliovirus, norovirus, rotavirus, hepatitis A, hepatitis, B, hepatitis C, dengue virus, varicella-zoster virus, herpes simplex virus, cytomegalovirus, Japanese encephalitis virus, West Nile virus, Zika virus, *Haemophilus influenzae* type b, measles virus, mumps virus, rubella virus, respiratory syncytial virus, influenza virus, yellow fever virus, rabies virus, smallpox virus, parvovirus, Chikungunya virus, *Corynebacterium diptheriae, Clostridium tetani, Clostridium botulinum, Bordetella pertussis, Streptococcus pneumoniae, Neisseria meningitides, Salmonella* spp., *Bacillus anthraces, Yersinia* spp., or a combination thereof.

6. The immunogenic-agent containing particle according to claim 1, wherein the at least one immunogenic agent comprises one or more antigens from canine parvovirus, canine distemper virus, canine adenovirus, rabies virus, canine parainfluenza virus, canine influenza virus, canine corona virus, measles virus, *Bordetella bronchiseptica, Leptospira* spp., *Borrelia burgdorferi*, or a combination thereof.

7. The immunogenic-agent containing particle according to claim 1, wherein the at least one immunogenic agent comprises one or more antigens from feline herpesvirus 1, feline calicivirus, feline panleukopenia virus, rabies virus, feline leukemia virus, feline immunodeficiency virus, virulent systemic feline calicivirus, *Chlamydophila felis, Pasteurella haemolytica, Bordetella bronchiseptica*, or a combination thereof.

8. The immunogenic-agent containing particle according to claim 1, wherein the at least one immunogenic agent comprises one or more antigens from Eastern equine encephalomyelitis virus (EEEV), Western equine encephalomyelitis virus (WEEV), Venezuelan equine encephalomyelitis virus (VEEV), rabies virus, Chikungunya virus, West Nile virus, equine influenza virus, equine herpesvirus, *Streptococcus equi equi, Clostridium tetani, Neorickettsia risticii, Clostridium tetani*, or a combination thereof.

9. The immunogenic-agent containing particle according to claim 1, wherein the at least one immunogenic agent comprises one or more antigens from bovine herpesvirus, parainfluenza type 3 virus, bovine viral diarrhea virus, bovine respiratory syncytial virus, *Clostridium chauvoei, Clostridium septicum, Clostridium novyi, Clostridium perfringens* type C, *Clostridium perfringens* type D, *Pasteurella haemolytica, Clostridium haemolyticum*, Chikungunya virus, or a combination thereof.

10. The immunogenic-agent containing particle according to claim 1, wherein the at least one immunogenic agent comprises one or more antigens from Marek's disease virus, reovirus, avian encephalomyelitis virus, avian influenza virus, avipoxviruses, chicken anemia virus, *Pasteurella multocida*, Newcastle disease virus, *Riemerella anatipestifer*, duck herpesvirus 1, duck hepatitis virus, or a combination thereof.

11. The immunogenic-agent containing particle according to claim 1, wherein the at least one immunogenic agent comprises one or more antigens from *Cryptococcus* spp., *Aspergillus* spp., *Blastomyces* spp., *Candida albicans, Paracoccidioides* spp., *Sporothrix* spp., *Histoplasma capsulatum, Pneumocystis jirovecii, Coccidioides immitis*, or a combination thereof.

12. The immunogenic agent-containing particle according to claim 1, wherein the at least one immunogenic agent comprises a multimeric protein complex.

13. The immunogenic agent-containing particle according to claim 1, wherein the at least one glass-forming agent comprises at least one of trehalose, sucrose, ficoll, dextran, maltotriose, lactose, mannitol and glycine, hydroxyethyl starch, glycine, cyclodextrin, povidone and a combination thereof.

14. The immunogenic agent-containing particle according to claim 2, wherein the at least one smoothing excipient comprises at least one of hydroxyethyl starch, serum albumin, human serum albumin, dextran, hetastarch, plasma protein factor, or a combination thereof.

15. The immunogenic agent-containing particle according to claim 1, wherein each layer of the one or more coating layers comprises one or more of aluminum oxide ($Al_2O_3$), an aluminum alkoxide or a combination of different layers in the immunogenic agent-containing particle of aluminum oxide ($Al_2O_3$) and an aluminum alkoxide.

16. A method of making immunogenic agent-containing particles according to claim 1, the method comprising:
   combining at least one immunogenic agent with at least one glass-forming agent to form a primary liquid immunogenic composition;
   dehydrating the primary liquid immunogenic composition to form immunogenic agent-containing glassy microparticles wherein the at least one immunogenic agent is in an essentially dried glassy state; and
   coating the immunogenic agent-containing glassy microparticles with one or more coating layers to form immunogenic agent-containing particles, wherein each layer of the one or more coating layers comprises one or more of aluminum oxide ($Al_2O_3$), an aluminum alkoxide, silicon dioxide ($SiO_2$), titanium dioxide ($TiO_2$), and silicon nitride ($Si_3N_4$).

17. The method according to claim 16, wherein the primary liquid immunogenic composition further comprises at least one smoothing excipient.

18. An immunogenic composition comprising a plurality of immunogenic agent-containing particles according to claim 1.

19. An immunogenic composition comprising a standard immunogenic composition against a pathogen and a plurality of immunogenic agent-containing particles according to claim 1, wherein the at least one immunogenic agent-containing particles is capable of eliciting a boost immune response to the standard immunogenic composition against the pathogen.

20. An immunogenic composition comprising:
   a plurality of first immunogenic agent-containing particles according to claim 1, wherein the first immunogenic agent-containing particles comprise at least a first immunogenic agent;

a plurality of second immunogenic agent-containing particles according to claim 1, wherein the second immunogenic agent-containing particles comprises at least a second immunogenic agent different from the first immunogenic agent; and a pharmaceutically acceptable excipient.

21. A kit comprising at least one immunogenic agent-containing particle according to claim 1 and at least one container.

22. The immunogenic composition according to claim 1, wherein the immunogenic composition comprises a pharmaceutical composition and further comprises a pharmaceutically acceptable excipient.

23. The immunogenic composition according to claim 3, wherein the pathogenic virus, the peptide or the polypeptide derived from the pathogenic virus, the recombinant molecule derived from the pathogenic virus, the inactivated pathogenic virus, or chimera comprises a non-enveloped virus, an enveloped virus, an RNA virus or a DNA virus.

\* \* \* \* \*